(12) United States Patent
Bierbach et al.

(10) Patent No.: US 9,765,103 B2
(45) Date of Patent: Sep. 19, 2017

(54) CLEAVABLE CONJUGATES OF FUNCTIONALIZED PLATINUM-ACRIDINE AND PLATINUM-BENZACRIDINE AGENTS AND METHODS THEREOF

(71) Applicant: WAKE FOREST UNIVERSITY, Winston-Salem, NC (US)

(72) Inventors: Ulrich Bierbach, Winston Salem, NC (US); Song Ding, Durham, NC (US)

( * ) Notice: Subject to any disclaimer, the term of this patent is extended or adjusted under 35 U.S.C. 154(b) by 0 days.

(21) Appl. No.: 15/321,578

(22) PCT Filed: Jun. 22, 2015

(86) PCT No.: PCT/US2015/036892
§ 371 (c)(1),
(2) Date: Dec. 22, 2016

(87) PCT Pub. No.: WO2015/200172
PCT Pub. Date: Dec. 30, 2015

(65) Prior Publication Data
US 2017/0210772 A1    Jul. 27, 2017

Related U.S. Application Data

(60) Provisional application No. 62/015,478, filed on Jun. 22, 2014, provisional application No. 62/136,562, filed on Mar. 22, 2015.

(51) Int. Cl.
*A61K 31/555* (2006.01)
*C07F 15/00* (2006.01)

(52) U.S. Cl.
CPC ................. *C07F 15/0093* (2013.01)

(58) Field of Classification Search
CPC ............................. A61K 31/555; C07F 15/00

USPC ............................................ 514/185; 546/10
See application file for complete search history.

(56) References Cited

PUBLICATIONS

Graham, L. A. et al.: Synthesis, aqueous reactivity, and biological evaluation of Carboxylic acid ester-functionalized Platinum-Acridine hybrid anticancer agents. J. of Med. Chem., vol. 55, pp. 7817-7827, 2012.*

* cited by examiner

*Primary Examiner* — Charanjit Aulakh
(74) *Attorney, Agent, or Firm* — Ben Schroeder Law PLLC

(57) ABSTRACT

The present invention relates to using a versatile synthetic approach to generate a new class of ester, amido, or carbamate prodrugs of highly potent, but systemically too toxic, platinum-acridine anticancer agents. The new hybrids contain a hydroxyl group, which has been masked with a cleavable lipophilic acyl moiety. Both butanoic (butyric) and bulkier 2-propanepentanoic (valproic) esters were introduced to these compounds. The goal of this design was to improve the drug-like properties of the pharmacophore (e. g., log D) without compromising its DNA-mediated cell kill potential. Two distinct pathways by which the target compounds undergo effective ester hydrolysis, the proposed activating step, have been confirmed: platinum-mediated, self-immolative ester cleavage in a low-chloride environment (LC-ESMS, NMR spectroscopy) and enzymatic cleavage by human carboxylesterase-2 (hCES-2) (LC-ESMS). Several of the new compounds show excellent stability, reduced systemic toxicity, and favorable activation profiles while maintaining submicromolar cytotoxicity in various cancers, such as lung adenocarcinoma cell lines (A549, NCI-H1435). The results suggest that the novel dual-mode prodrug concept may have the potential to hasten the preclinical development of platinum-acridines.

20 Claims, 7 Drawing Sheets

CLEAVABLE CONJUGATES OF FUNCTIONALIZED PLATINUM-ACRIDINE AND PLATINUM-BENZACRIDINE AGENTS AND METHODS THEREOF

The present application claims priority under 35 USC 119(e) to U.S. Provisional Application Nos. 62/015,478 filed Jun. 22, 2014, and 62/136,562, filed Mar. 22, 2015, the entire contents of both of which are incorporated by reference in their entireties.

This work was supported at least in part by the National Institutes of Health/NCI (Grant CA101880). Accordingly, the Federal Government has rights in the instant invention.

FIELD OF THE INVENTION

The present invention relates to a novel series of platinum acridine agents with an ester, carbamate, and/or amide moieties that have exquisite potency for treating certain types of cancer. The compounds show excellent stability, reduced systemic toxicity, and favorable activation profiles while maintaining submicromolar cytotoxicity to certain cancers. Because of the profiles of the compounds, they are expected to have extended circulation time, reduce premature renal clearance, and selective cleavage/deprotection properties relative to currently existing compounds.

BACKGROUND OF THE INVENTION

Traditional chemotherapies often suffer from high systemic toxicity and a narrow therapeutic window. To improve the pharmacokinetics (PK) and toxicity profiles of anticancer drugs, various avenues are being pursued, such as nano-sized delivery platforms, receptor-targeted conjugates, and prodrug designs. The rationale behind the latter approach is to generate a precursor molecule, which is converted post administration to the actual bioactive form of the drug enzymatically or in response to a chemical stimulus. Bioactivation may occur during absorption, circulation, or at the tumor site. The benefits of lipophilic prodrugs include efficient retention in, and absorption from, circulation, as well as improved penetration of membranes and accumulation in target tissues.

DNA-targeted platinum-acridine hybrid agents have shown exquisite potency in several solid tumor models. Particularly, non-small cell lung cancer (NSCLC) cells prove to be extremely sensitive to this pharmacophore. Unlike cisplatin and its analogues, platinum-acridines derived from PTACRAMTU (1) do not cross-link DNA bases but produce structurally unique hybrid adducts that are an intrinsically more severe form of DNA damage than the former bifunctional adducts. However, despite their promising cell kill in chemoresistant, intractable cancers, many of the currently existing platinum-acridine compounds show unfavorable ADME (absorption, distribution, metabolism, and excretion) properties, which slow their preclinical development.

The prototype compound 1', for instance, while inhibiting the growth of xenografted NCI-H460 tumors in mice, showed signs of severe toxicity in the test animals, resulting in a low maximum tolerated dose (MTD). Mice necropsied after treatment with 1' showed high levels of platinum in normal tissues, but insufficient accumulation in tumors, as well as discoloration of the kidneys, a possible sign of hepatotoxicity or nephrotoxicity.

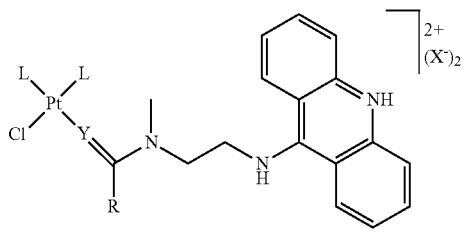

1 (PT-ACRAMTU): $L_2$ = en, Y = S, R = NHMe, X = Cl or $NO_3$
1': L = $NH_3$, Y = NH, R = Et, X = Cl or $NO_3$
1'': L = en, Y = NH, R = Me, X = Cl or $NO_3$
1''': L = pn, Y = NH, R = Me, X = Cl or $NO_3$

Chart 1. General Structure of First- and Second-Generation Platinum-Acridine Hybrid Agents Compound 1 (PT-ACRAMTU, Chart 1; ACRAMTU=1-[2-(acridin-9-ylamino)ethyl]-1,3-dimethylthiourea) represents the prototype of a class of DNA-targeted platinum-acridine hybrid agents, which have shown exquisite potency in several solid tumor models. Non-small cell lung cancer (NSCLC) cells prove to be particularly sensitive to this pharmacophore, with the newer derivatives showing $IC_{50}$ values in NSCLC cell lines in the low-nanomolar range and activity in tumor xenografts. Using a classical structure-activity relationship (SAR) approach and modular library screening, the chemical stability could be tuned and the off-target reactivity of the pharmacophore could be reduced. Some desired improvements were achieved by modifying the ligand and donor sets around the electrophilic metal. These efforts have led to the development of a derivative (1''', Chart 1) that shows higher potency than cisplatin by three orders of magnitude (the $IC_{50}$ values for 1''' in NCI-H460 and A549 lung cancer cells were 1.3 and 3.9 nM, respectively).

The promising cell kill results in chemoresistant, intractable cancers, platinum-acridines yet the unfavorable ADME (absorption, distribution, metabolism, and excretion) properties, has made the development of modified compounds imperative. The compounds, which currently exist, such as compound 1', for instance, while inhibiting the growth of xenografted NCI-H460 tumors in mice, showed signs of severe toxicity in test animals, resulting in a low maximum tolerated dose (MTD). Mice necropsied after treatment with compound 1' showed high levels of platinum in normal tissues, but insufficient accumulation in tumors, as well as discoloration of the kidneys, a possible sign of hepatotoxicity or nephrotoxicity. It is with these drawbacks in mind that the present invention was developed.

BRIEF SUMMARY OF THE INVENTION

In one embodiment, the present invention relates to platinum-acridine compounds that possess improved pharmacological properties. These platinum-acridine compounds open the therapeutic window for systemic treatment with these agents.

To improve the pharmacological properties of platinum-acridines and to open the therapeutic window for systemic treatment with these agents, the present invention relates to newly designed lipophilic ester-based prodrugs that can be specifically tuned to undergo chemical or enzymatic hydrolysis in circulation, during absorption, or directly in cancer tissue. This new concept has resulted in the first case of a platinum-containing agent that is recognized as a substrate by human carboxylesterase-2 (hCES-2), a key enzyme involved in the activation of several anticancer prodrugs.

The technology presented in this disclosure can be considered the most important step in promoting platinum-acridines from bench to bedside.

Moreover, the compounds of the present invention show $IC_{50}$ values in NSCLC cell lines in the low-nanomolar range and activity in tumor xenografts.

The compounds of the present invention may also have potential use as antiviral or anti-Alzheimer compounds.

DETAILED DESCRIPTION OF THE INVENTION

Figure 1:
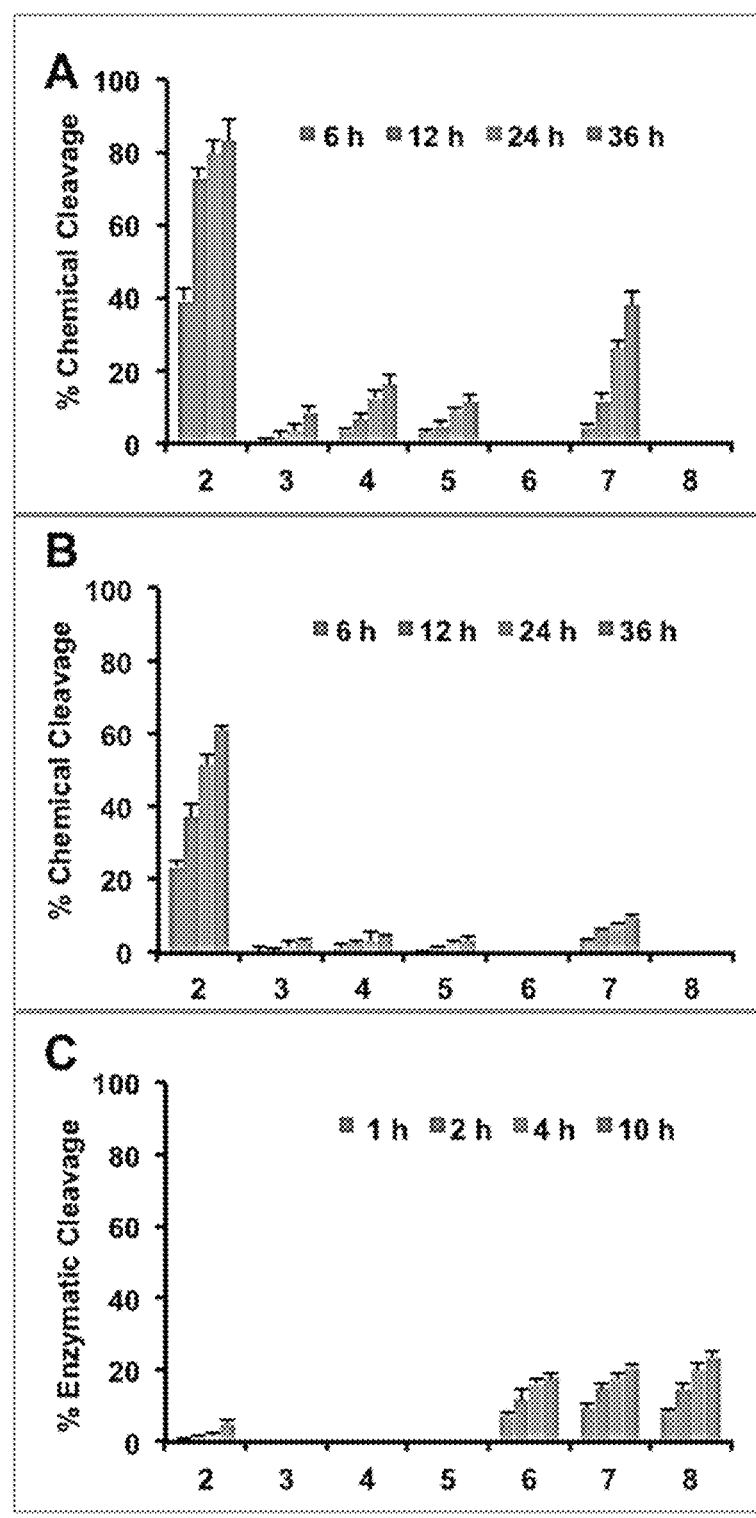
FIG. 1 shows the cleavage of ester moieties in compounds 2-8 monitored by quantitative HPLC for hydrolysis reactions in phosphate buffer, PB, pH 7.4 (panel A), phosphate-buffered saline, PBS, pH 7.4 (panel B), and in PBS in the presence of hCES-2 (panel C). Plotted data are the mean of three incubations ± standard deviations. Yields of conversion for compound 7 in panel C represent the sum of chemical (minor) and enzymatic (major) cleavage, which produced indistinguishable products. Reactions were performed at 37° C.

In one embodiment, the present invention relates to platinum-acridine compounds that possess improved pharmacological properties. These platinum-acridine compounds open the therapeutic window for systemic treatment with these agents. In an embodiment, these lipophilic ester-based pro-drugs/compounds can be specifically tuned to undergo chemical or enzymatic hydrolysis in circulation, during absorption, or directly in cancer tissue. This new concept has resulted in the first case of a platinum-containing agent that is recognized as a substrate by human carboxylesterase-2 (hCES-2), a key enzyme involved in the activation of several anticancer prodrugs. The technology presented in this disclosure should be considered one of the most important steps in promoting platinum-acridines from bench to bedside.

Moreover, the compounds of the present invention show $IC_{50}$ values in NSCLC cell lines in the low-nanomolar range and activity in tumor xenografts.

The compounds of the present invention may also have potential use as antiviral or anti-Alzheimer compounds.

Accordingly, in an embodiment, the present invention relates to compounds, compositions and methods using compounds of the formula I shown below.

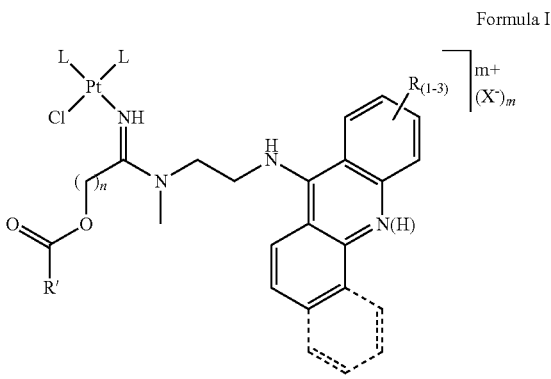

Formula I wherein each L independently is $NH_3$ or the Ls together with the platinum atom to which they are attached form a ring made up of an aliphatic diamine;
R is independently H, $NO_2$, or halo;
R' is a primary alcohol, a secondary alcohol or tertiary alcohol group containing between 1 and 10 carbon atoms, or alternatively between 7 and 10 carbon atoms, or alternatively between 1 and 8 carbon atoms, or alternatively between 1 and 6 carbon atoms, or a primary, secondary, or tertiary alkyl group that contains a carboxylic acid group or an amido functionality; or an aryl group that contains an alcohol, carboxylic acid or amido group. R' may also be an alkyl-aryl or an aryl group that contains an alcohol, carboxylic acid, or amido group which may additionally be optionally substituted with one or more substituents such as halo, hydroxyl, carboxyl, nitro, amino, $C_{1-6}$alkyl, $C_{2-6}$alkenyl, or $C_{2-6}$alkynyl;
n is 1 to 6;
m is 1 or 2;
and X is halo or $NO_3$.

In an embodiment, R' may be linked to functionalities derived from natural or synthetic products such as succinic acid, glycolic acid, or 3-hydroxypropionic acid;

In an embodiment, R' may be linked to functionalities derived from natural or synthetic products such as primary, secondary alkyl and/or aryl amines that contain an alcohol or carboxylic acid or fatty acid amines, aniline, piperidine; or polymers such as chitosan; or miscellaneous bioactive molecules such as Rucaparib or Endoxifen.

In an embodiment, R' may be a group that is derived from compounds that contain an alcohol (to generate an ester) or a primary or secondary amine (to generate an amide). For example, compounds that may be used that generate the functionality that becomes R' include succinic acid, Endoxifen, certain tyrosine kinase inhibitors, Rucaparib, DPPE phospholipid, aninoazide, o-methylarginine, and certain fatty acid amines. The following are examples of compounds that can become R' wherein the primary or secondary amino functionality or the alcohol functionality is used as the reactive site to generate the compounds of the present invention.

For example if succinic acid is used, the following generic structure is indicative of the compounds that can be generated:

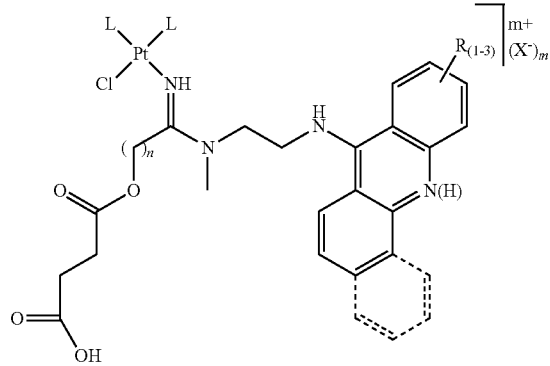

In some embodiments, the following three structures were generated. These structures were confirmed and/or characterized by NMR and by LCMS.

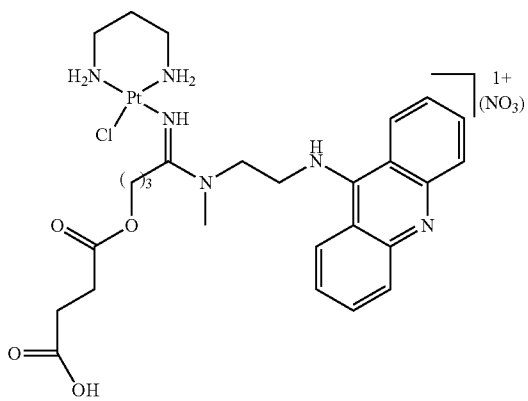

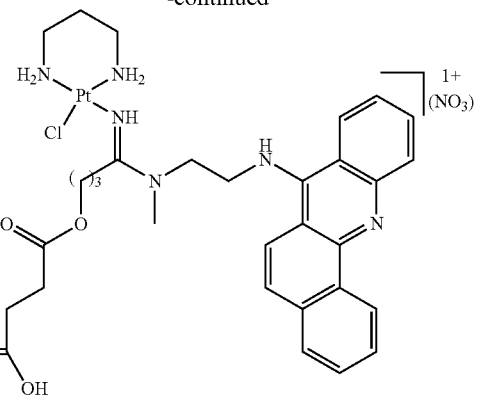

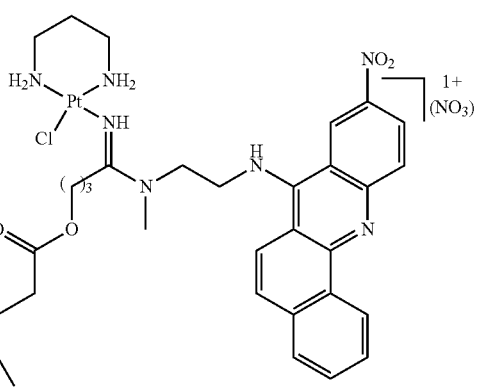

In an embodiment, compounds with a primary or secondary amine that will become the amide included as a part of R' include:

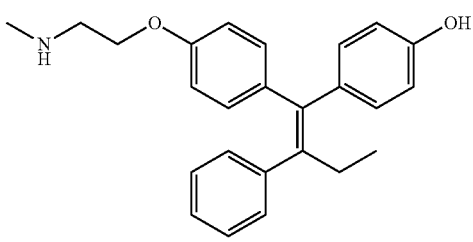

(E/Z)-Endoxifen

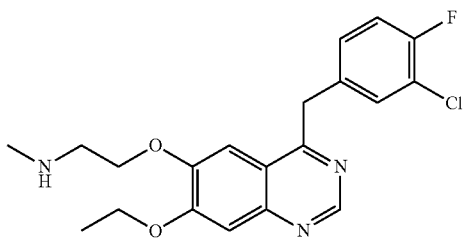

A tyrosine kinase inhibitor

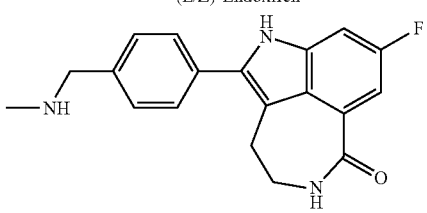

Rucaparib

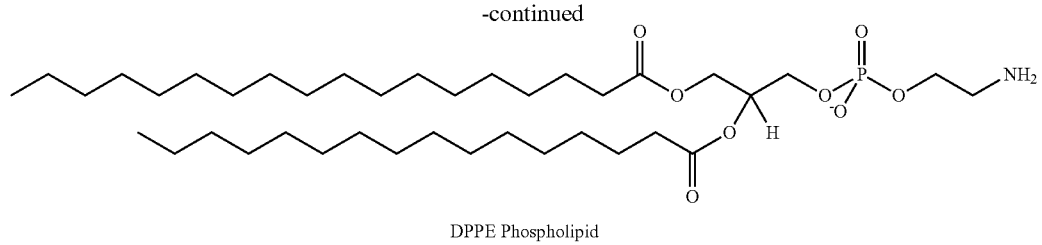
DPPE Phospholipid
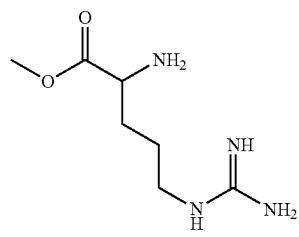
Aminoazide        Fatty Amine
O-Methylarginine
In an embodiment, compounds that fit within the scope of the present invention include the endoxifen moiety as R' or some of the other above compounds such as:
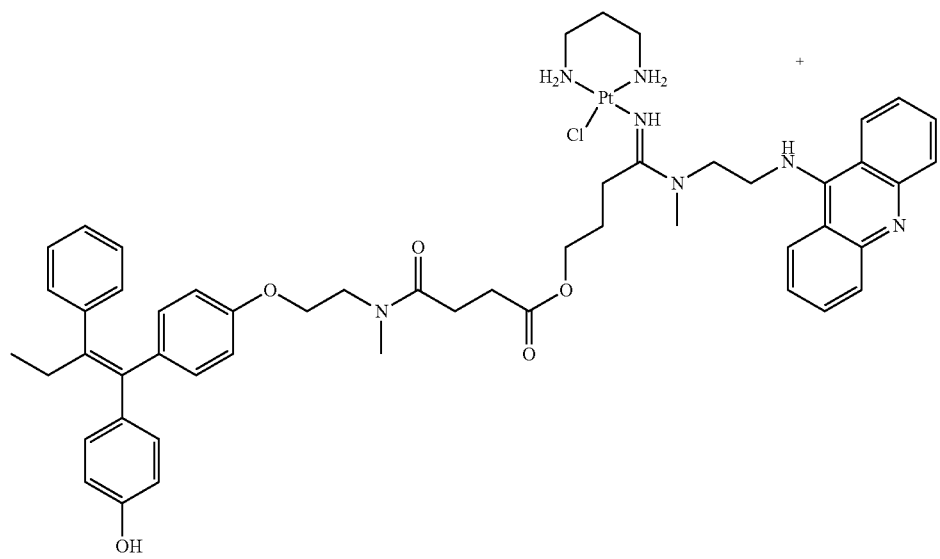
Molecular Weight: 1096.65

-continued
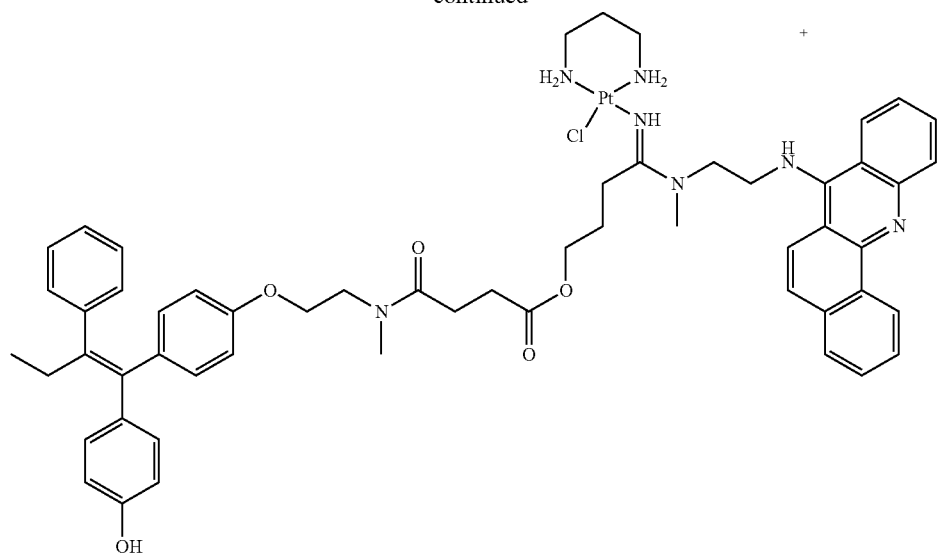
Molecular Weight: 1146.71
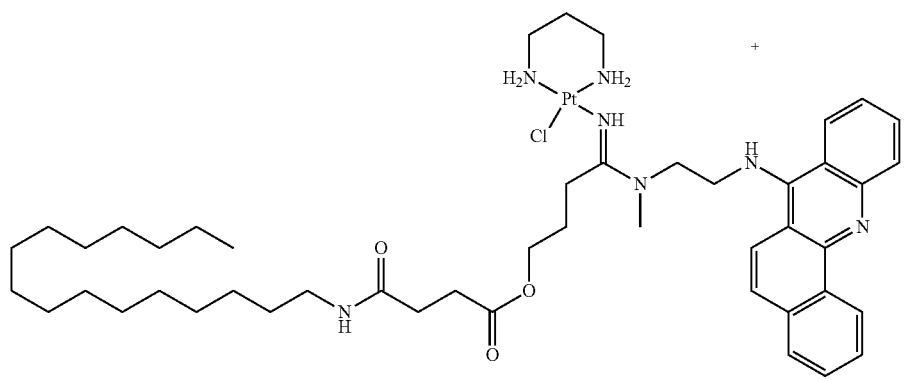
Molecular Weight: 1014.68
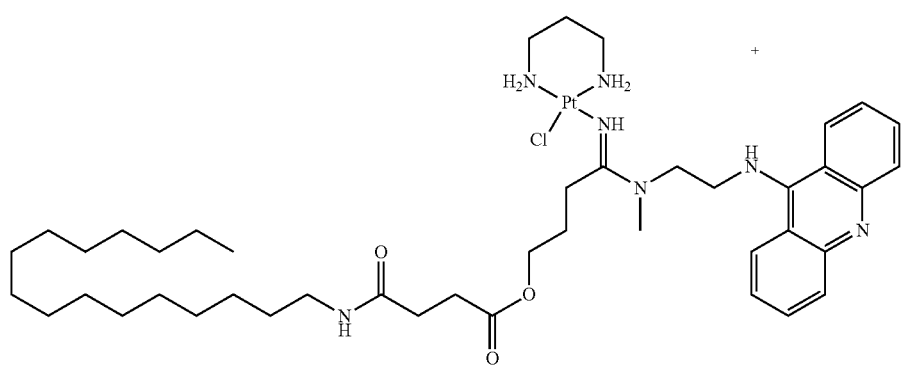
Molecular Weight: 964.62

-continued

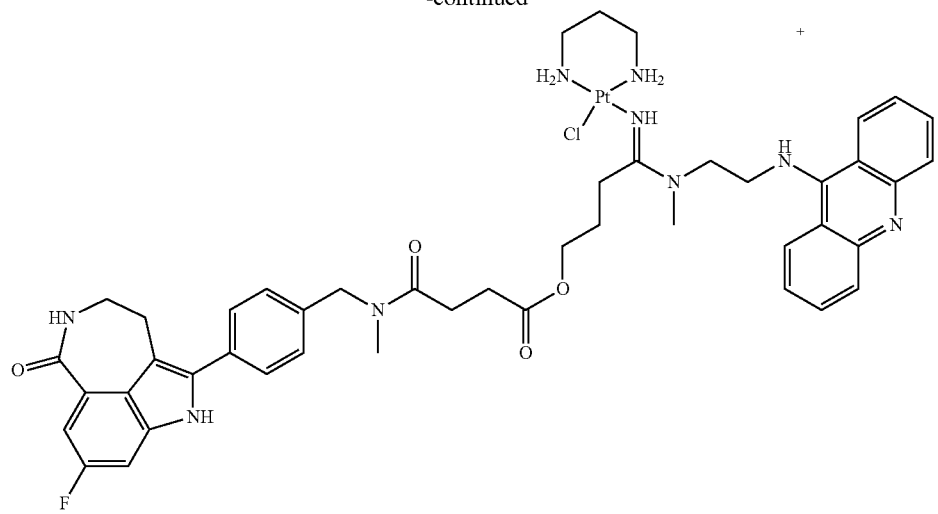

Molecular Weight: 1046.53

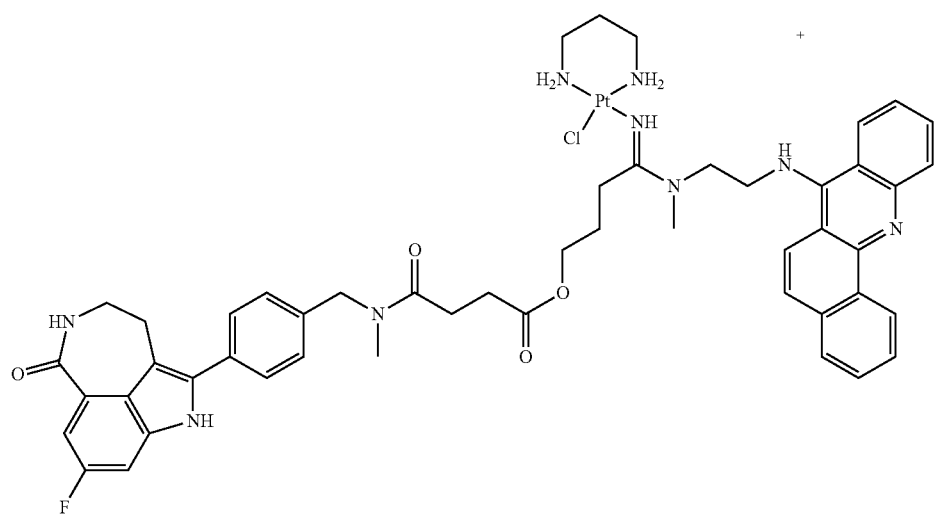

Molecular Weight: 1096.59

The above structures were confirmed and/or characterized by NMR and/or LCMS.

It should be understood that a wide variety of compounds that contain an alcohol, a primary or secondary amine may be useful to deliver intact the platinum compounds of the present invention. These compounds may then undergo accelerated hydrolysis upon delivery to cancer cells.

In one embodiment, when the Ls in the Formula I form a ring with the platinum compound to which they are joined, the Ls may be aliphatic diamines such as ethane-1,2-diamine, propane-1,3-diamine, trans-1,2-diaminocyclohexane (R,R, S,S, and R,S isomers), 2,3-diaminobutane (R,R, S,S, and R,S isomers), and other similar functional groups.

In an embodiment, R' may be a linear alkyl group such n-propyl (butyric acid); a branched symmetrical alkyl group such as 2-propylpentyl (valproic acid); a branched asymmetrical alkyl group such as 3-methyl-n-butyryl, 2-methyl-n-valeryl. In a variation, R' may be a cyclic group such as cyclopropyl, cyclobutyl, cyclopentyl, cyclohexyl, cycloheptyl, cyclooctyl, or cyclononyl. In a variation, R' may be saturated or unsaturated fatty acids such as oleic acid, linolic, stearic, DHA (Docosahexaenoic acid), or EPA (Eicosapentaenoic acid). In a variation, R' may contain oligopeptides such as the residues in RGD (Arg-Gly-Asp), poly-Glutamic acid, or poly-Aspartic acid. In a variation, R' may be dendrimers, or miscellaneous bioactive natural products. Alternatively, R' may contain some or all of the moieties present in syalic acid, oleanolic acid, folic acid, and/or salicylic acid.

In an embodiment, R' may be propyl or 4-yl heptyl.

In an embodiment, n is 1 to 3. In a variation, n is 1. In a variation, n is 3.

In an embodiment, X is Cl or $NO_3$. In a variation, X is $NO_3$.

In an embodiment, the Ls are amino groups or together with the platinum atom to which they are attached, the Ls form the ring —$NH_2$—$(CH_2)_v$—$NH_2$— wherein v is 1, 2, 3, or 4 or both Ls together can be any of the following groups a-h;

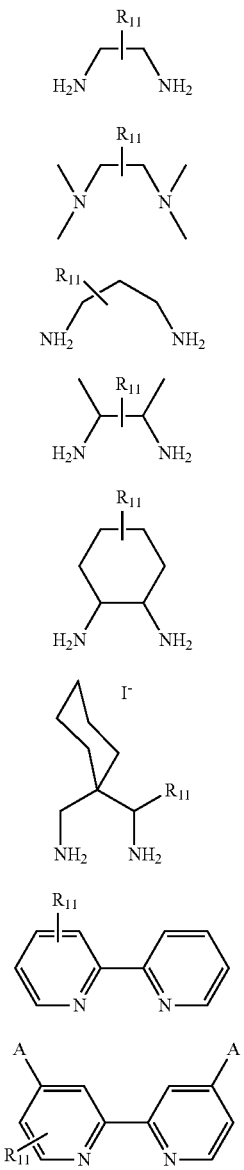

wherein each A is independently H, —CH$_3$, —OCH$_3$, CF$_3$ or NO$_2$; and wherein R$_{11}$ is a halo, hydroxyl, carboxyl, nitro, amino, C$_{1-6}$alkyl, C$_{2-6}$alkenyl, C$_{2-6}$alkynyl, —OCH$_3$, or CF$_3$.

In an embodiment, the compounds of Formula I may be used in pharmaceutical compositions and/or in methods to treat cancers. The methods may be used in subjects that are need of treatment. The methods may be used to treat cancers that include lung cancer, testicular cancers, ovarian carcinomas, head and neck cancers, leukemias and lymphomas. In an embodiment, the cancer is lung adenocarcinoma.

The pharmaceutical composition may contain pharmaceutically acceptable salts, solvates, and prodrugs thereof, and may contain diluents, excipients, carriers, or other substances necessary to increase the bioavailability or extend the lifetime of the compounds of the present invention.

Subjects that may be treated by the compounds and compositions of the present invention include, but are not limited to, horses, cows, sheep, pigs, mice, dogs, cats, primates such as chimpanzees, gorillas, rhesus monkeys, and, humans. In an embodiment, a subject is a human in need of cancer treatment.

The pharmaceutical compositions containing a compound of the invention may be in a form suitable for injection either by itself or alternatively, using liposomes, micelles, and/or nanospheres.

The pharmaceutical composition suitable for injection can be made as disclosed in Lammers, T. et al., J. Controlled Release, 161, 175-187 (2012), or in Barenholz, Y., J. Controlled Release, 160, 117-134, (2012), both of which are incorporated by reference in their entireties. Alternatively, compositions intended for injection may be prepared according to any known method, and such compositions may contain one or more agents selected from the group consisting of solvents, co-solvents, solubilizing agents, wetting agents, suspending agents, emulsifying agents, thickening agents, chelating agents, antioxidants, reducing agents, antimicrobial preservatives, buffers, pH adjusting agents, bulking agents, protectants, tonicity adjustors, and special additives. Moreover, other non-toxic pharmaceutically-acceptable excipients which are suitable for the manufacture of injectables may be used.

Aqueous suspensions may contain the active compounds in an admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, condensation products of ethylene oxide with long chain aliphatic alcohols, for example, heptadecaethyl-eneoxycethanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

In an embodiment, the present invention relates to compounds, compositions, and methods that are ideally suited for oral delivery. The residue R' imparts lipophilicity to Formula I, which renders the molecules very favorable for oral delivery.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, sterile water for injection (SWFI), Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

Thus, in another embodiment, the present invention provides a pharmaceutical formulation solution comprising a compound of Formula I or a salt thereof.

A solution of the invention may be provided in a sealed container, especially one made of glass, either in a unit dosage form or in a multiple dosage form.

Any pharmaceutically acceptable salt of a compound of Formula I may be used for preparing a solution of the invention. Examples of suitable salts may be, for instance, the salts with mineral inorganic acids such as hydrochloric, hydrobromic, sulfuric, phosphoric, nitric and the like, and the salts with certain organic acids such as acetic, succinic, tartaric, ascorbic, citric, glutamic, benzoic, methanesulfonic, ethanesulfonic and the like. In an embodiment, the compound of Formula I is a hydrochloric acid salt including a mono, di, or trihydrochloride.

Any solvent which is pharmaceutically acceptable and which is able to dissolve the compounds of Formula I or a pharmaceutically acceptable salt thereof may be used. The solution of the invention may also contain one or more additional components such as a co-solubilizing agent (which may be the same as a solvent), a tonicity adjustment agent, a stabilizing agent, a preservative, or mixtures thereof. Examples of solvents, co-solubilizing agents, tonicity adjustment agents, stabilizing agents and preservatives which may suitable for a solution formulation are described below.

Suitable solvents and co-solubilizing agents may include, but are not limited to, water; sterile water for injection (SWFI); physiological saline; alcohols, e.g. ethanol, benzyl alcohol and the like; glycols and polyalcohols, e.g. propyleneglycol, glycerin and the like; esters of polyalcohols, e.g. diacetine, triacetine and the like; polyglycols and polyethers, e.g. polyethyleneglycol 400, propyleneglycol methylethers and the like; dioxolanes, e.g. isopropylidenglycerin and the like; dimethylisosorbide; pyrrolidone derivatives, e.g. 2-pyrrolidone, N-methyl-2-pyrrolidone, polyvinylpyrrolidone (co-solubilizing agent only) and the like; polyoxyethylenated fatty alcohols; esters of polyoxyethylenated fatty acids; polysorbates, e.g., Tween™, polyoxyethylene derivatives of polypropyleneglycols, e.g., Pluronics™.

Suitable tonicity adjustment agents may include, but are not limited to, pharmaceutically acceptable inorganic chlorides, e.g. sodium chloride; dextrose; lactose; mannitol; sorbitol and the like.

Preservatives suitable for physiological administration may be, for instance, esters of parahydroxybenzoic acid (e.g., methyl, ethyl, propyl and butyl esters, or mixtures of them), chlorocresol and the like.

Suitable stabilizing agents include, but are not limited to, monosaccharides (e.g., galactose, fructose, and fucose), disaccharides (e.g., lactose), polysaccharides (e.g., dextran), cyclic oligosaccharides (e.g., alpha-, beta-, gamma-cyclodextrin), aliphatic polyols (e.g., mannitol, sorbitol, and thioglycerol), cyclic polyols (e.g. inositol) and organic solvents (e.g., ethyl alcohol and glycerol).

The above mentioned solvents and co-solubilizing agents, tonicity adjustment agents, stabilizing agents and preservatives can be used alone or as a mixture of two or more of them in a solution formulation.

In an embodiment, a pharmaceutical solution formulation may comprise a compound of Formula I or a pharmaceutically acceptable salt thereof, and an agent selected from the group consisting of sodium chloride solution (i.e., physiological saline), dextrose, mannitol, or sorbitol, wherein the agent is in an amount of less than or equal to 5%. The pH of such a formulation may also be adjusted to improve the storage stability using a pharmaceutically acceptable acid or base.

In the solutions of the invention the concentration of the compound of Formula I or a pharmaceutically acceptable salt thereof may be less than 100 mg/mL, or less than 50 mg/mL, or less than 10 mg/mL, or less than 10 mg/mL and greater than 0.01 mg/mL, or between 0.5 mg/mL and 5 mg/mL, or between 1 mg/mL and 3 mg/mL. In an embodiment, the concentration that is used is the ideal concentration to be sufficiently cytotoxic to the cancer cells yet limit the toxicity on other cells.

Suitable packaging for the pharmaceutical solution formulations may be all approved containers intended for parenteral use, such as plastic and glass containers, ready-to-use syringes and the like. In an embodiment, the container is a sealed glass container, e.g. a vial or an ampoule. A hermetically sealed glass vial is particularly preferred.

According to an embodiment of the present invention, there is provided, in a sealed glass container, a sterile, injectable solution comprising a compound of Formula I or a pharmaceutically acceptable salt thereof in a physiologically acceptable solvent, and which has a pH of from 2.5 to 3.5. For solution formulations, various compounds of the present invention may be more soluble or stable for longer periods in solutions at a pH lower than 6. Further, acid salts of the compounds of the present invention may be more soluble in aqueous solutions than their free base counter parts, but when the acid salts are added to aqueous solutions the pH of the solution may be too low to be suitable for administration. Thus, solution formulations having a pH above pH 4.5 may be combined prior to administration with a diluent solution of pH greater than 7 such that the pH of the combination formulation administered is pH 4.5 or higher. In one embodiment, the diluent solution comprises a pharmaceutically acceptable base such as sodium hydroxide. In another embodiment, the diluent solution is at pH of between 10 and 12. In another embodiment, the pH of the combined formulation administered is greater than 5.0. In another embodiment, the pH of the combined formulation administered is between pH 5.0 and 7.0.

The invention also provides a process for producing a sterile solution with a pH of from 2.5 to 3.5 which process comprises dissolving a compound of Formula I or a pharmaceutically acceptable salt thereof in a pharmaceutically acceptable solvent. Where a pharmaceutically acceptable acid salt of a compound of Formula I is used the pH of the solution may be adjusted using a pharmaceutically acceptable base or basic solution adding a physiologically acceptable acid or buffer to adjust the pH within a desired range. The method may further comprise passing the resulting solution through a sterilizing filter.

One or more additional components such as co-solubilizing agents, tonicity adjustment agents, stabilizing agents and preservatives, for instance of the kind previously specified, may be added to the solution prior to passing through the sterilizing filter.

In a further variation, the present invention contemplates combination therapies in which the compounds of the present invention can be used in conjunction with other cisplatin compounds. The efficacy of this combination therapy is likely to be enhanced because of the different mechanisms and modes of action that first generation cisplatin compounds exhibit relative to the compounds of the present invention. It is also contemplated and therefore within the scope of the invention that other anti-neoplastic agents/compounds can be used in conjunction with the compounds of the present invention. The anti-neoplastic agents/compounds that can be used with the compounds of the present invention include cytotoxic compounds as well as non-cytotoxic compounds.

Examples include anti-tumor agents such as HERCEPTIN™ (trastuzumab), RITUXAN™ (rituximab), ZEVALIN™ (ibritumomab tiuxetan), LYMPHOCIDE™ (epratuzumab), GLEEVAC™ and BEXXAR™ (iodine 131 tositumomab).

Other anti-neoplastic agents/compounds that can be used in conjunction with the compounds of the present invention include anti-angiogenic compounds such as ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGER inhibitory agents (e.g., antibodies or antigen binding regions that specifically bind thereto) such as ABX-EGF (panitumumab), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto).

Other anti-angiogenic compounds/agents that can be used in conjunction with the compounds of the present invention include Campath, IL-8, B-FGF, Tek antagonists, anti-TWEAK agmets (e.g., specifically binding antibodies or antigen binding regions, or soluble TWEAK receptor antagonists, ADAM distingrin domain to antagonize the binding of integrin to its ligands, specifically binding anti-eph receptor and/or anti-ephrin antibodies or antigen binding regions, and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Other ami-angiogenic/anti-tumor agents that can be used in conjunction with the compounds of the present invention include: SD-7784 (Pfizer, USA); cilengitide, (Merck KGaA, Germany, EPO 770622); pegaptanib octasodium, (Gilead Sciences, USA); Alphastatin, (BioActa, UK); M-PGA, (Celgene, USA); ilomastat, (Arriva, USA,); emaxanib, (Pfizer, USA,); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC; antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland); the ARGENT technology of Ariad, USA; YIGSR-Stealth, (Johnson & Johnson, USA); fibrinogen-E fragment, (BioActa, UK); the angiogenesis inhibitors of Trigen, UK; TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (WVAX, USA); Benefin, (Lane Labs, USA); Tz-93, (Tsumura, Japan); TAN-1120, (Takeda, Japan); FR-111142m (Fujisawa, Japan); platelet factor 4, (RepliGen, USA); vascular endothelial growth factor antagonist, (Borean, Denmark); bevacizumab (pINN), (Genentech, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS 1404, (Cancer Research Laboratory, New Zealand); SG 292, (Telios, USA); Endostatin, (Boston Children's Hospital, USA); ATN 161, (Attenuon, USA); ANGIOSTATIN, (Boston Children's Hospital, USA); 2-methoxyestradiol, (Boston Children's Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering AG, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478,(ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Children's Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrugs, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS 100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pIN), (Genaera, USA); RPI 4610, (Sima, USA); heparanase inhibitors, (InSight, Israel); KL 3106, (Kolon, South Korea); Honokiol, (Emory University, USA); ZK CDK, (Sobering AG, Germany); ZK Angio, (Schering AG, Germany); ZK 229561, (Novartis, Switzerland, and Schering AG, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Fik-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin I inhibitor, (Allegheny Health, Education and Research Foundation, USA).

It is contemplated and therefore within the scope of the invention that the compounds of the present invention can be modified to target specific receptors or cancer cells or can be modified so that they can survive various in vivo environments.

In a further variation, the compounds of the present invention can be used against solid tumors, cell lines, and cell line tissue that demonstrate upregulated nucleotide excision repair and other upregulated resistance mechanisms.

Design and Chemistry. Platinum-acridines may show excellent cytotoxicity but unfavorable drug-like properties. The most cytotoxic derivatives exist in their fully protonated [pKa(9-aminoacridine)≈9.5-10], dicationic form. Because these hybrids are too hydrophilic, they show poor tissue distribution and are most likely removed too rapidly from circulation via renal clearance. Based on this supposition, the goal of the structural modifications introduced here was to increase the lipophilicity of the agents while maintaining good water solubility. The alkyl residue of the amidine donor group (residue R, for Y=NH, see Chart 1) was chosen as the site of attachment for the carboxylic acid ester groups. The design involved installation of a hydroxymethyl (MeOH) or an extended 3-hydroxypropyl (Pr3—OH) group as R in place of simple Me and Et in 1'-1''' and masking of the terminal OH function as lipophilic esters in the corresponding prodrug (see Scheme 1). A primary carboxylic acid, butanoic (butyric) acid, and a branched secondary carboxylic acid, 2-propylpentanoic (valproic) acid, were introduced as acyl components (see Scheme 1). The latter residue has previously been utilized in an amide-protected prodrug of the anticancer drug gemcitabine, which is cleaved by hCES-2.11

As an additional potential benefit of this design, bulky, hydrophobic ester groups installed on the DNA-binding pharmacophore may be incompatible with the hydrophilic DNA major groove and slow the formation of cytotoxic adducts, supporting the idea of an inactive prodrug. By contrast, molecular models generated for the DNA adduct of the active form of the hybrid agent containing the "deprotected" Pr3—OH linker show the terminal hydroxyl group in hydrogen bonding distance to DNA phosphate, which may favor DNA binding.

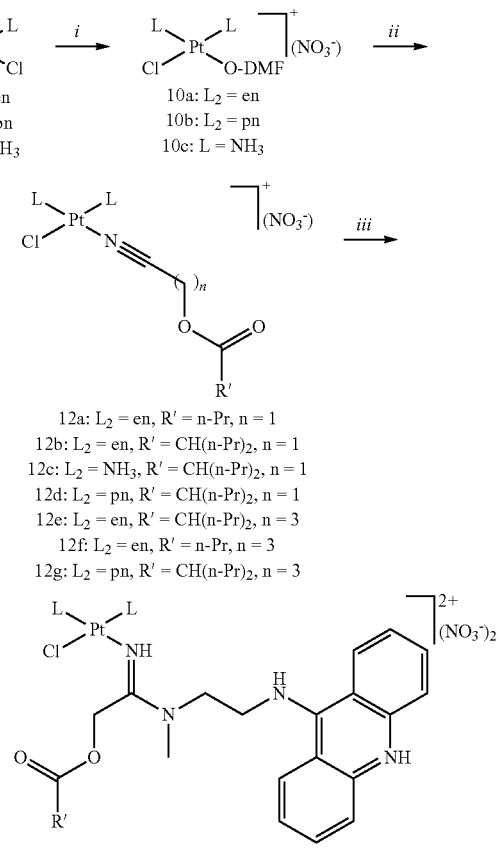

Scheme 1. Synthesis of Target Compounds

Reagents and conditions: (i) AgNO3, DMF, rt: (ii) appropriate nitrile-ester (11a-d), DMF, 60° C., 4 h, (iii) (1) 13, DMF, 4° C., (2) 1 M HNO3. Abbreviations: en=ethane-1,2-diamine, pn=propane-1,3-diamine.

Two distinct mechanisms of prodrug activation are proposed: chemical and enzymatic hydrolysis. The former mechanism has previously been observed in chemically related carboxylic acid-modified platinum-acridines containing a reversed ester linkage (Pt-linker—C(O)OR', instead of Pt-linker—OC(O)R' used in this invention). It involves platinum-assisted ester cleavage in a chloride-ion concentration dependent manner. Low intracellular chloride is proposed to favor aquation of platinum, which serves as a Lewis-acidic metallohydrolase. The significantly higher chloride concentration in circulation would suppress loss of chloro ligand and quench ester hydrolysis. The second mode of activation involves ubiquitous carboxylesterase isoenzymes, in particular hCES-2, which is not only expressed at high levels in the gastrointestinal tract and the liver, but also in tumor tissue.1 The choice of hCES-2 rather than hCES-1 as the target enzyme was based on the well-documented substrate selectivity of the two forms, according to which hCES-2 preferentially recognizes esters containing bulky alcohols (here, the hydroxyl-modified hybrid agent itself) in combination with relatively smaller acyl moieties.

A total of seven ester-protected hybrids were synthesized. Structural diversity in this set of compounds was achieved by varying the chain length, n, and the nature of the acyl residue, R' (Scheme 1). In addition, different non-leaving amines (L) were introduced to tune the reactivity of the platinum moiety (see discussion below). Compounds 2-8 were generated from the platinum precursors (12a-g) containing the appropriate ester-modified nitrile ligands (11a-g). The ligand substitution reactions leading to the precursor complexes containing short-chain nitrile-esters (n=1, 12a-d) produced significantly lower yields than reactions performed with the long-chain derivatives (n=3, 12e-g) (20-30% vs. 80-90%). This previously observed effect can be attributed to the high CH acidity of the nitrile ligands in the former set of derivatives, which leads to undesired complex dimerization.12 Likewise, attempts to generate analogous derivatives with n=2 failed due to unexpected β-elimination of the hydroxyl group (data not shown). The final step affording hybrid agents 2-8 (yield >75%, analytical purity >95%) involved addition of the NHMe group in N-(acridin-9-yl)-N'-methylethane-1,2-diamine (13) across the metal-activated nitrite triple bond, producing the desired amidine linkage, and subsequent protonation to generate the dinitrate salts. An anomaly in the stereochemistry of the addition reactions leading to hybrids 2-5 was observed. The extended-chain ester derivatives (6, 7, and 8) and the prototype (1') almost exclusively (>90%) exist as E-isomers in which the platinum moiety and amidine-NMe group adopt a trans configuration with respect to the N(imino)=C double bond, as typically observed in amidine ligands formed from secondary amines. By contrast, hybrids 2-5 form a relatively high amount of the Z-isomer (>25%, based on 1-D and 2-D NMR analysis). This outcome can be attributed to the increased steric hindrance produced by the short-chain (n=1) acyl groups around the nitrile group. Intramolecular hydrogen bonding between the imino proton and the ester group (NH•••O=C—O) may also contribute to this effect.

All newly synthesized hybrids maintain excellent solubility of >10 mg/mL in relevant aqueous media. To demonstrate the effect of the pendant ester groups on the hydrophilicity/lipophilicity balance of the compounds, the partitioning of selected derivatives wa studied between octanel and phosphate-buffered saline (PBS) (expressed as log[coctanol/cPBS]=log D, the distribution coefficient for protonable pharmacophores). The experiment was performed in PBS at pH 7.4 rather than water to suppress complex aquation and platinum-mediated ester hydrolysis as described in the following section. This setup also takes into consideration the pH dependence of log D to faithfully mimic conditions in plasma. For the unmodified, hydrophilic agent, 1', a log D of −0.98 (±0.19) was determined. By contrast, compound 8, the presumably most lipophilic derivative (n=3, valproic ester, L=pn), preferentially partitions into the octanol phase with a log D of 0.73 (±0.06), which reflects an increase in lipophilicity by 50-fold relative to compound 1'. An intermediate log D of −0.31 (±0.06) was determined for compound 7 (n=3, L=en, butyric ester). The log D value generated for this compound, however, has to be interpreted with caution because of unavoidable partial ester hydrolysis under the conditions of the experiment (<10%, see the following section).

Metal-Assisted Ester Hydrolysis. One of the proposed mechanisms of activation of compounds 2-8 as prodrugs involves platinum-promoted ester cleavage. To mimic the chloride ion concentration differential that exists between serum during circulation and after uptake into target cells, compounds were incubated at 37° C. in PBS (~150 mM NaCl pH 7.4) and in phosphate buffer (PB, pH 7.4), respectively, The reaction mixtures were analyzed at appropriate time points by in-line high-performance liquid chromatography-electrospray mass spedrometry (LC-ESMS). Reaction products were identified as 1+ or 2+ charged molecular ions in mass spectra recorded in positive-ion mode and quantified by integration of UV-visible HPLC traces at an acridine-specific wavelength.

The time course of ester hydrolysis yielding hydroxyl-modified platinum-acridine and butyric/valproic acid is summarized for both media in FIG. 1. Generally, in sets of analogues characterized by common spacers linking the platinum and ester moieties (n), the valproic esters show significantly slower conversion than the butyric esters, or no conversion at all (3-5 vs. 2, and 6, 8 vs. 7). In phosphate-buffered solution in the absence of chloride (FIG. 1A), the most extensive hydrolysis is observed for butyric ester-based compounds 2 (n=1) and 7 (n=3), with the former producing approximately two-fold higher levels of cleavage product after 36 h of continuous incubation. Hydrolytic activity is also observed for the valproic ester derivatives 3, 4, and 5 (all n=1), but at a much slower rate. Most strikingly, hybrids 6 and 8, which contain the same secondary acyl moiety but on an extended linker (n=3), are completely resistant to cleavage under these conditions. When incubations were performed in buffer supplemented with physiological chloride, a major reduction in ester hydrolysis of up to 75% was observed (FIG. 1B) compared to reactions in chloride-free media, consistent with the notion that (reversible) aquation of the platinum moiety plays a role in the cleavage mechanism.

Figure 2:
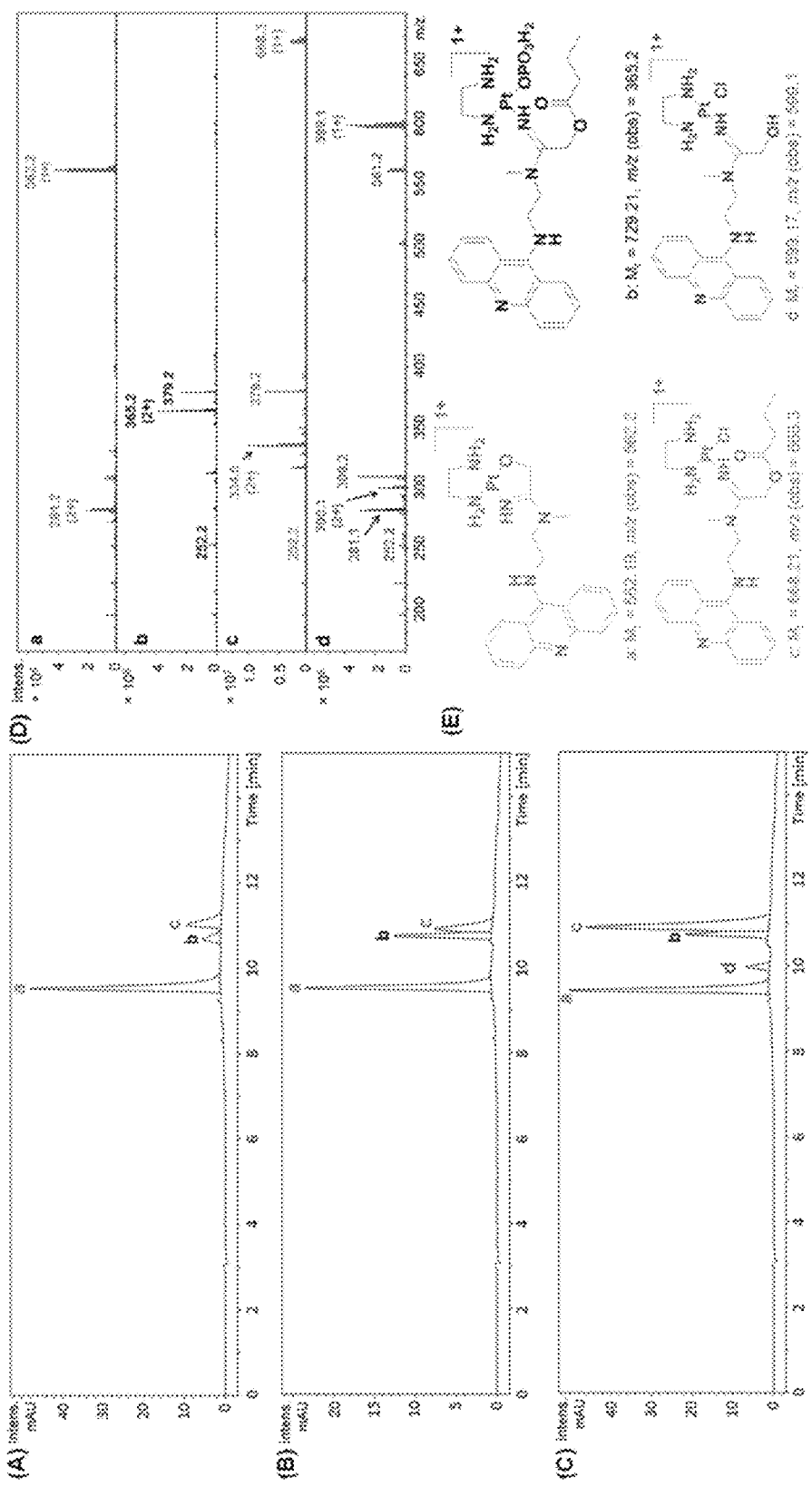
FIG. 2 shows reverse-phase HPLC traces for the separation of reaction products resulting from ester cleavage in compound 2 in PB (A), in PBS (B), and by hCES-2 (C). Mass spectra recorded in positive-ion mode for fractions labeled a-d and the corresponding structures and m/z values of the molecular ions are given in panels D and E, respectively
Figure 3:
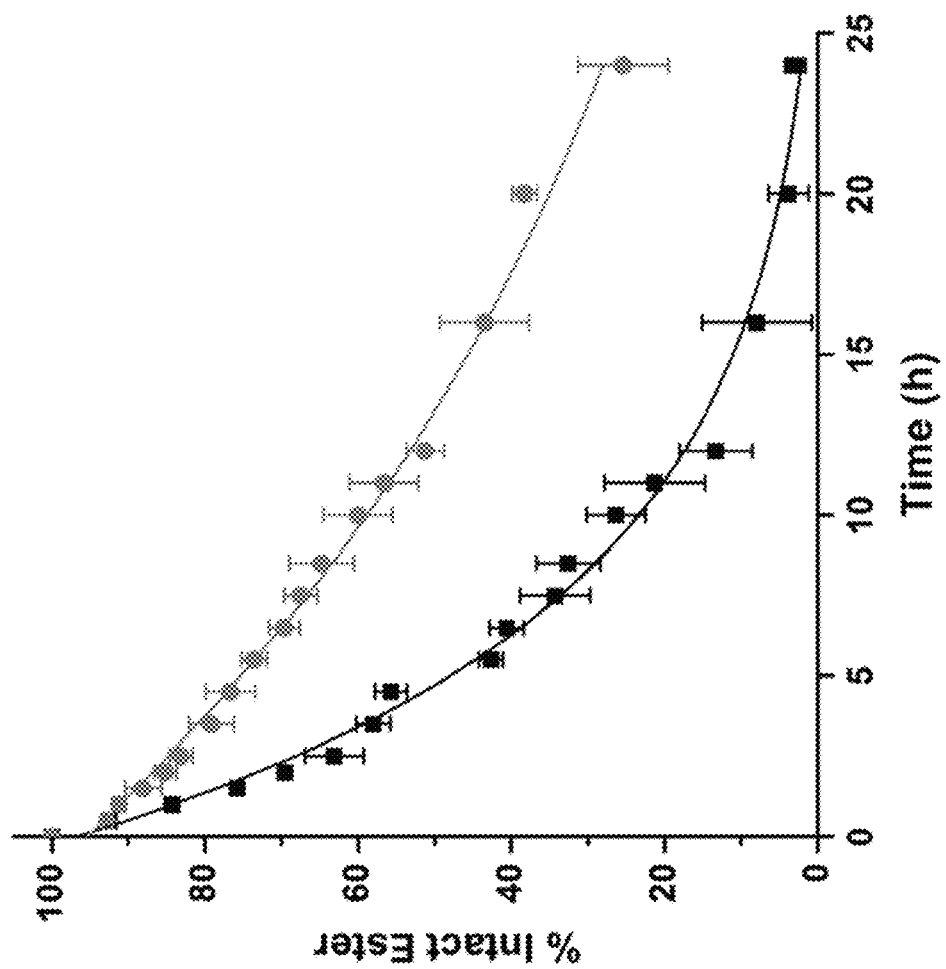
FIG. 3 shows the kinetics of ester hydrolysis in compound 2 monitored by 1H NMR spectroscopy [D2O, pH* 7.0, 2 mM Pt in 10 mM PB (black trace) or PBS (red trace)] at 37° C. for 24 h. The data sets were fitted to the first-order exponential decay function y=y0+A e-x/t, where t−1 is the rate constant, k [h−1], and x is the reaction time, t [h]. Data points represent means of at least three integrated signal intensities ± standard deviations. The experiment was performed in duplicate with similar results.

The LC-ESMS profiles of compounds 2-5 share common features and support the proposed mechanism of platinum-mediated ester cleavage. Compound 2 was chosen for a kinetic study by 1H NMR spectroscopy and for a detailed discussion. The only hydrolysis product formed in incubations of compound 2 in PB was identified as a chelate in which the chloro leaving group has been replaced with the unprotected hydroxyl oxygen of the cleaved butyric ester (see peak labeled 'a' in FIG. 2A and the corresponding mass spectrum/structure in FIGS. 2D/E, respectively). A minor amount of chemically unchanged compound 2 and a product resulting from substitution of chloride by phosphate containing intact ester are also observed after 36 h of incubation (peaks b and c). The same array of products was observed when compound 2 was incubated in the presence of sodium chloride in PBS, but ester cleavage and chelate formation were significantly suppressed based on the relative abundances of each species (FIG. 2B). The absence of an opened-chelate form in this high-chloride environment attests to the inertness of the five-membered amidine-N/hydroxyl-O chelate. This was also confirmed in incubations with biological nitrogen and sulfur model nucleophiles, in which this product was completely unreactive (data not shown). Unlike compounds 2-5 (n=1), compound 7 (n=3) exclusively forms hydrolysis products containing a dangling hydroxyl group, indicating that formation of a seven-membered, presumably less stable, chelate is disfavored. The dramatic effect of chloride ion on the kinetics of ester hydrolysis was confirmed for compound 2 in arrayed 1H NMR experiments. Cleavage of the butyric ester follows a (pseudo-) first-order rate law with rate constants of k=3.9× 10-5 s$^{-1}$ in PB and k=1.2×10$^{-5}$ s$^{-1}$ in PBS, which corresponds to half-lives of 5 h and 16 h, respectively (FIG. 3). Thus, chloride slows cleavage of the pendant ester in complex 2 by approximately 70%. On the basis of the above product analysis, a mechanism of platinum-mediated, intramolecular ester cleavage is proposed (Scheme 2).

Cleavage is triggered by (reversible) aquation of the platinum complex. The Lewis-acidic metal assists in the deprotonation of the aqua to a hydroxo ligand, which undergoes a nucleophilic attack on the acyl carbon to promote cleavage of the ester linkage. Cleavage results in the loss of the acyl protecting group as carboxylic acid and in a dangling or chelated alcohol/alkoxide moiety. High chloride concentrations shift the aquation reaction toward the chloro-substituted hybrid, which quenches ester cleavage. An intramolecular attack by platinum-associated hydroxide is also supported by the following observations: (i) hydrolysis of ester is approximately twice as efficient for complex 4 bearing ammine (NH3) non-leaving groups than for the en-substituted analogue 3. This effect is consistent with the lower pKa value of the aqua ligands in Pt-ammine than in Pt-en complexes, which produces higher concentrations of the more reactive hydroxo ligand. (ii) For derivatives containing the same acyl moiety, ester cleavage is dramatically reduced for n=3 vs. n=1. This effect can be rationalized with the fact that internal nucleophilic attack by the hydroxo ligand in the former compound requires formation of a 9-membered, thermodynamically less favorable, macrocyclic intermediate.

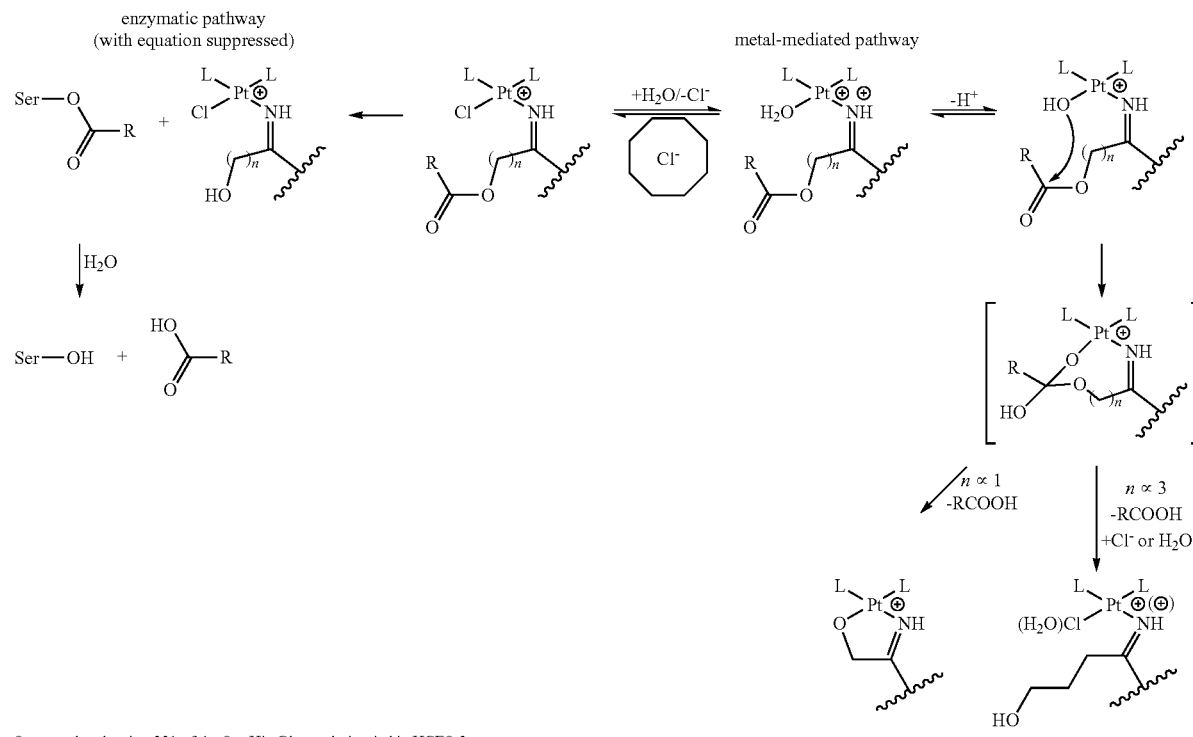

Scheme 2. Proposed Mechanisms of Chemical and Enzymatic Ester Cleavage

Ser = acylated serine-221 of the Ser-His-Glu catalytic triad in HCES-2
R = n-Pr (butyrate) or CH(n-Pr)$_2$ (valproate)

Ester Cleavage by Human Carboxylesterase-2 (hCES-2). To determine if compounds 2-8 are susceptible to deesterification by a pharmacologically relevant prodrug-converting enzyme, incubations were performed with recombinant human carboxylesterse-2 (hCES-2). The particular engineered form of the protein used was sufficiently robust to provide enzymatic activity over long reaction times (>30 min), which allows for identification of cleavage products for non-classical, slowly metabolized substrates. Reactions were performed in a buffer supplemented with chloride to suppress non-enzymatic hydrolysis and monitored for a relatively short period of time to minimize the effects of loss of enzyme activity over time and chemical hydrolysis. Unavoidable contributions from the latter pathway have been subtracted, where possible, from the data presented in FIG. 1C. LC-ESMS analysis of the reaction mixtures shows minimal or no enzyme-mediated cleavage of ester for compounds 2 and 3-5, respectively, which contain short spacers (n=1). By contrast, derivatives 6-8 (n=3) undergo slow deesterification under these conditions with yields of ~20% at the 10-h time point. In particular, the bulky valproic esters in compounds 6 and 8, which are completely resistant to chemical hydrolysis, are efficiently cleaved by the enzyme. The HPLC trace recorded for compound 2 after 10 h of incubation with enzyme (FIG. 2C) shows the same reaction products formed in PB and PBS, as well as an additional peak (d, ~5%) not observed for chemical hydrolysis. Positive-ion mass spectra unequivocally identified this product as the platinum-chloro complex containing a dangling hydroxyl group (FIGS. 2D,E), consistent with non-metal-mediated cleavage.

Figure 4:
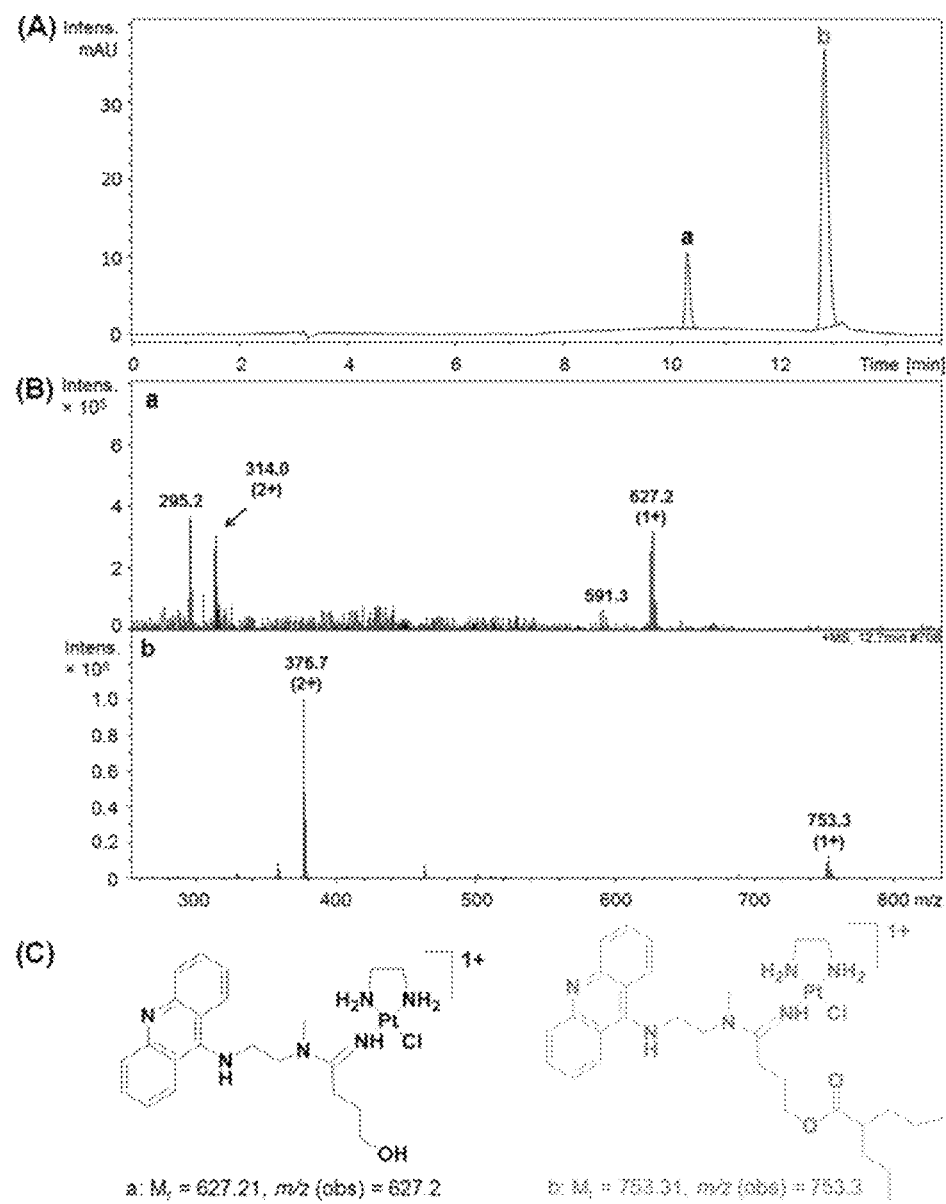
FIG. 4 shows Reverse-phase HPLC traces for the separation of reaction products resulting from ester cleavage in compound 8 by hCES-2 (A). Mass spectra recorded in positive-ion mode for fractions labeled a and b and the corresponding structures and m/z values of the molecular ions are given in panels B and C, respectively.

The fact that no opened chelate was detected for chemical hydrolysis of derivatives with n=1, but only five-membered N,O chelate, can he taken as evidence that the former must be an enzyme-specific product. Previous studies on cisptatin derivatives containing chelated aminoalcoholato ligands have demonstrated that their formation requires basic conditions to help deprotonate the alcohol, while opening of such chelates only occurs under acidic conditions. This is in agreement with the observation that the two forms (peaks a and d, FIG. 2C) do not interconvert under the conditions and on the time scale of the assay. Finally, unlike the butyric ester derivative 7, which shows dual cleavage reactivity resulting in the dangling hydroxyl form of the hybrid agent, the valproic ester derivatives 6 and 8 only undergo enzyme-mediated cleavage to produce the corresponding deesterified form (shown for compound 8 in FIG. 4). It can be concluded that only esters installed on an extended linker are viable substrates for hCES-2 and that only the chemically robust valproic ester confers true selectivity for enzymatic cleavage.

Figure 5:
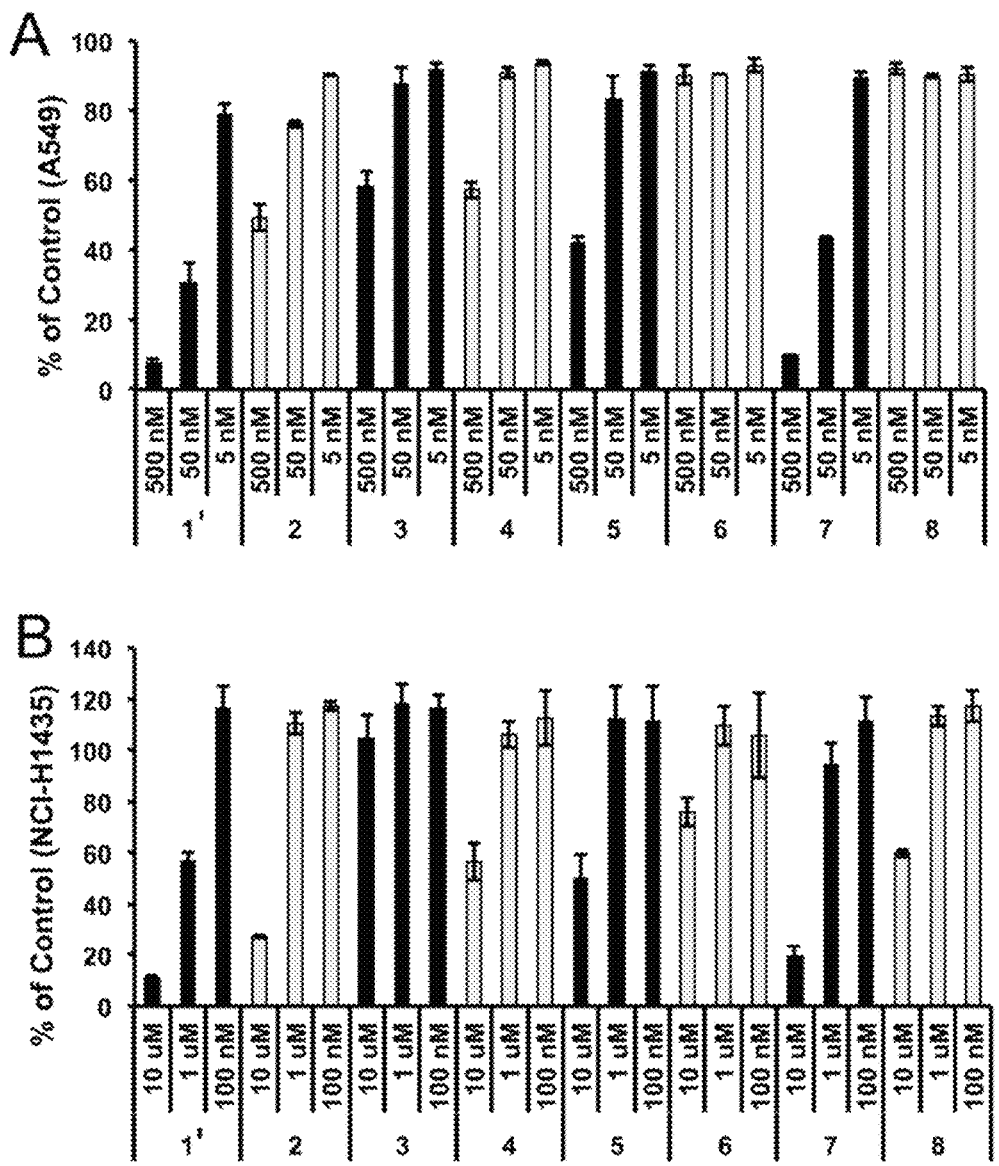
FIG. 5 shows the results of the chemosensitivity screen of compounds 1'-8 in A549 (A) and NCI-H1435 (B) cancer cells. Relative cell viabilities are means of two independent experiments performed in triplicate ± the standard deviation.
Figure 6:
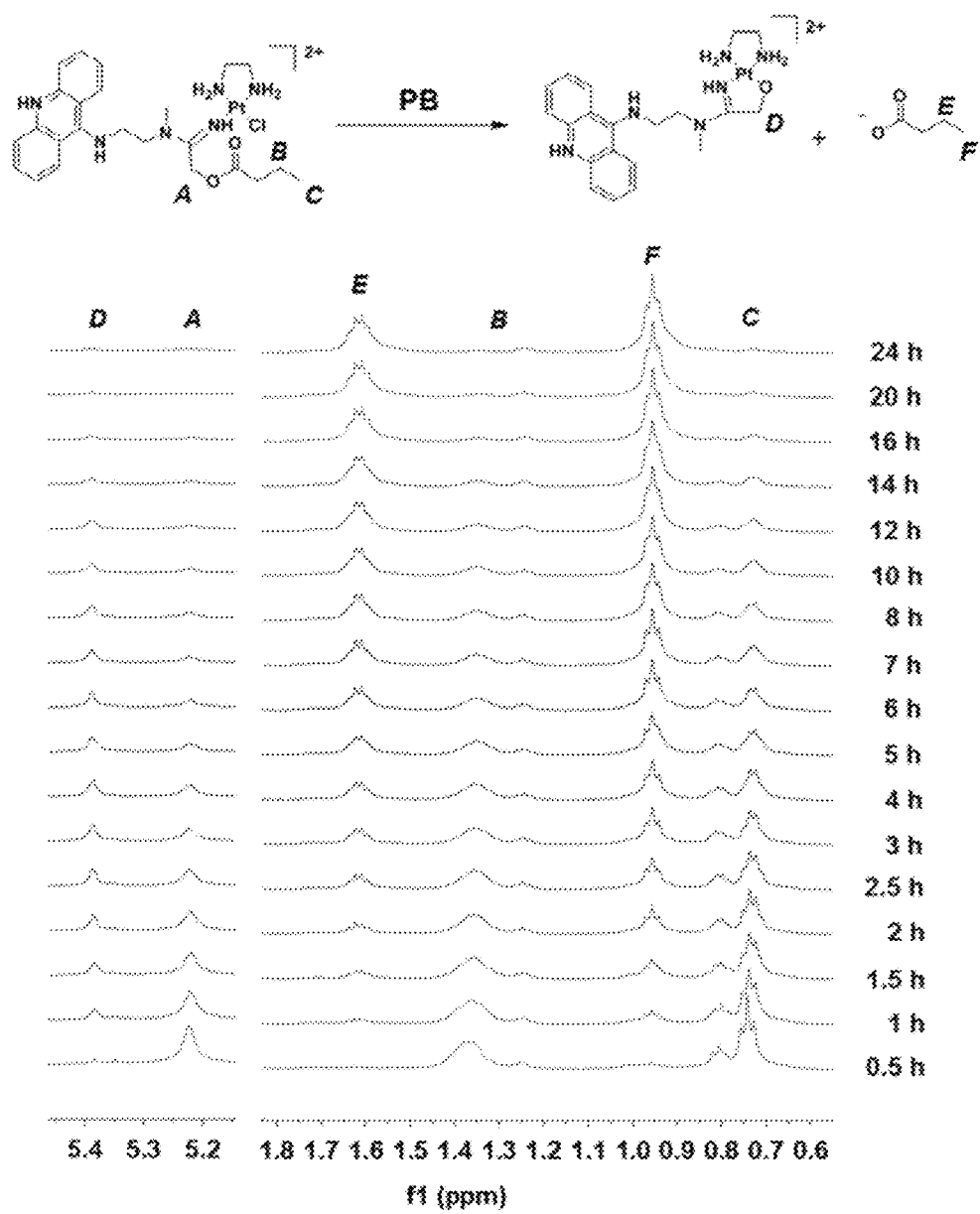
FIG. 6 shows a kinetic study using time-dependent $^1H$ NMR spectra for the hydrolysis reaction of complex 2 in 10 mM PB incubated at 37° C. The characteristic protons A, B and C of complex 2 were monitored to give signal assignments. Note the H.D exchange of the protons labeled 'D' due to the increase in CH acidity caused by electron-withdrawing platinum.
Figure 7:
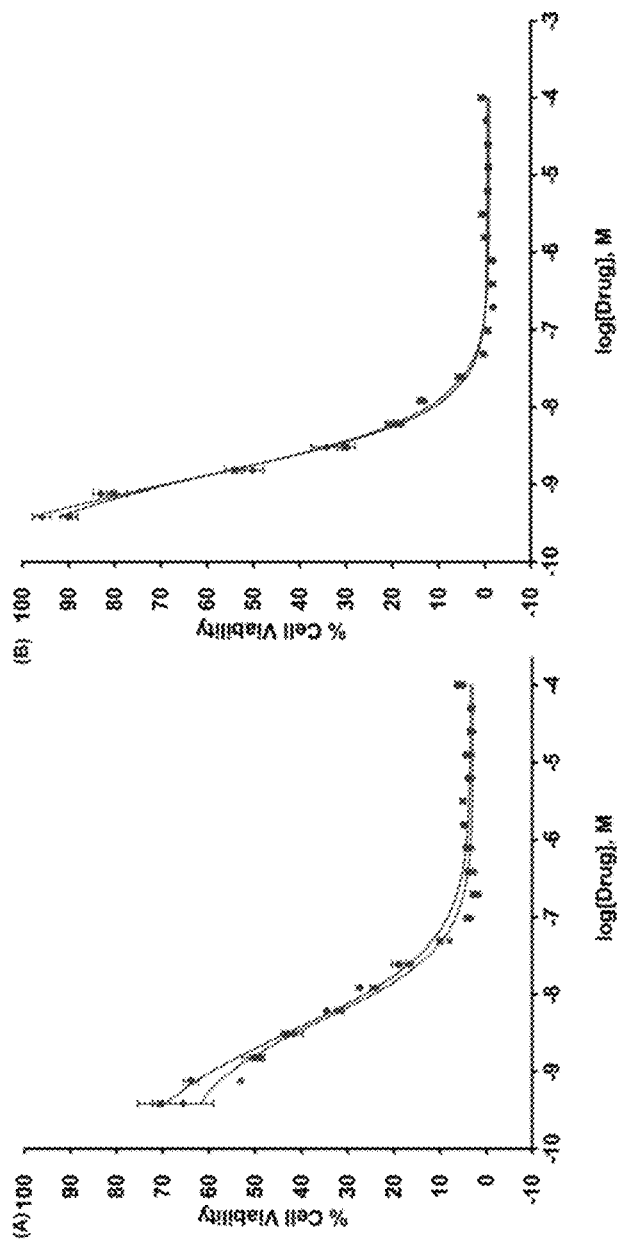
FIG. 7 shows drug-response curves for cell proliferation assays in non-small cell lung cancer cell lines (A) A549 and (B) NCI-H460 treated with compound 1'''. Error bars indicate ± standard deviations from the mean for two independent experiments performed in triplicate.

Cytotoxicity Studies. The cell kill properties of the newly generated compounds 2-8 were assessed using a colorimetric cell proliferation assay and compared to that of prototype 1' (chloride salt). (Note: attempts to synthesize the deesterified, proposed active hydroxyl forms of 2-8 in pure form for screening in this assay have been unsuccessful due to the chemical instability of the platinum-nitrile precursor complexes.) Two NSCLC adenocarcinoma cell lines were screened for chemosensitivity: A549, which responds well to treatment with platinum-acridines, and NCI-H1435, a DMA repair-proficient and highly chemoresistant form of this cancer. The latter cell line has also been shown to express significantly higher levels (>3-fold) of hCES-2 enzyme than A549 and other lung adenocarcinomas. Thus, cytotoxicity levels observed in the two cell lines may also provide hints about potential intracellular prodrug activation. Both cell lines were dosed with hybrid agents for 72 h at three selected concentrations, which were based on relative chemosensitivities established for compound 1'. A549 was dosed at 5.0, 50, and 500 nM, whereas 20-fold higher concentrations, 0.1, 1.0, and 10 □M, were chosen for NCI-H1435 to account for the relatively higher resistance observed in this cell line. The dose-response data resulting from the chemosensitivity screen are presented in FIG. 5.

As a general trend, the ester-modified derivatives show reduced cytotoxicity levels compared to the unmodified hybrid, 1', except for compound 7, which shows a response similar to that of the prototype in both cell lines. Because the butyrate-protected derivative is efficiently cleaved both chemically and enzymatically on a time scale relevant to the cell culture assay (see previous section), it is proposed that the hydroxyl form of this agent is the major contributor to the cell kill. It also suggests that the n-Pr3—OH residue in deesterified 7 in place of the Et residue in 1' does not compromise the potency of the pharmacophore, possibly pointing to a similar mechanism at the DNA adduct level. By contrast, the derivatives containing valproic ester show greatly reduced activity. Compound 6, for instance, which would generate the same active hydroxyl form as compound 7, and compound 8 show no cell kill in A549 at the highest dose and significantly reduced activity in NCI-H1435. This observation is in agreement with the less efficient intracellular cleavage of the bulkier valproic esters 6 and 8, which, in their intact form, are less cytotoxic possibly due to their inability to cause sufficiently high levels of adducts in nuclear DNA. The same trend is observed for compounds 3-5, which proved to be relatively resistant to chemical and enzymatic hydrolysis. For compounds sharing the same linkers and ester moieties, the nature of the non-leaving group had only minor or no effects on the activity. Finally, compound 2, whose butyrate ester is cleaved very efficiently in chloride-deprived media (see previous section), showed activity inferior to the prototype. This outcome was expected because of the substitution inertness of the 5-membered chelate generated in the process.

It appears that compounds 2, 6, and 8, which are cleaved by hCES-2, show a more pronounced enhancement in activity relative to compound 1' in NCI-H1435 (high hCES-2) than in A549 (low hCES-2). The opposite seems to be the case for compound 7. To assess if a relationship might exist between predicted cleavage mechanism and cytotoxicity in the two cell lines, the selectivity index, S, was defined as a measure of prodrug sensitivity: $S=[CV_i,NCI\text{-}H1435/CV1',NCI\text{-}H1435]/[CV_i,A549/CV1',A549]$, where $CV_i$ and $CV1'$ are the % viabilities of the ester-based compounds and compound 1' for their highest doses, respectively. CV1' was introduced to normalize for differences in chemosensitivities between the two cell lines. Assuming that CV1' is the highest cell kill that can be achieved with any of the activated ester prodrugs, S values smaller than '1' would indicate a relative advantage of a given derivative in NCI-H1435, and vice versa. For compounds 2, 6, 7, and 8, S values of 0.4, 0.6, 1.4, and 0.5 were calculated, respectively. It can be concluded that the prodrugs that are not cleaved chemically (6, 8) or converted to a presumably inactive chelate (2), but show hCRS-2-mediated cleavage, perform relatively better in NCI-H1435.

Conversely, compound 7, which can be converted to its active form via an enzyme-independent pathway, appears to have a relative advantage in A549. These findings may indicate that high levels of hCES-2 promote prodrug activation and confer sensitivity to NCI-H1435 cells for the chemically inert esters. It should be noted, however, that a direct comparison of prodrug responses between two different cell lines has to be interpreted with caution. Because cellular uptake and efflux, among other factors, may also contribute to the observed differences in cytotoxic responses, additional experiments in hCES-2 knockdown or hCES-2 transfected cells of the same type are necessary.

On the basis of their physicochemical properties, chemical reactivities, their ability to serve as hCES-2 substrates, and their performance in cell lines, compounds 7 and 8 are considered hits for future PK and efficacy studies. Both derivatives, which contain butyric or valproic esters on an extended linker, are promising prodrug candidates for slow cleavage by hCES-2. Compound 7 holds promise of providing a dual mode of prodrug cleavage, in which chemical activation may be necessary for applications requiring extended circulation of lipophilic prodrug in plasma followed by accelerated intracellular hydrolysis. By contrast, the more lipophilic and chemically less reactive analogue 8, should achieve even longer half-lives in circulation, but would require activation by target enzyme expressed in the liver (similar to the anticancer prodrug irinotecan) or in tumor tissue. Whether the butyric and valproic esters are prone to hydrolysis by other ubiquitous serum esterases remains to be determined. To this end, incubations of 2-8 with fetal bovine serum (FBS, Thermo Scientific HyClone), which is commonly used as a model for human serum, have failed to provide information on such unwanted reactivity. This is due to irreversible binding of platinum to the protein fraction in this assay (data not reported).

Another potential advantage of bulky prodrugs of platinum-acridines may be their poor DNA binding properties. If ester cleavage occurs primarily intracellularly in tumor tissue, differential DNA recognition by the ester-protected (inactive) and hydroxo (active) forms of the hybrid agent might confer prodrug selectivity to cancer cells while sparing normal cells. In addition to an improved ADME profile, lipophilic prodrugs also have the potential benefit of improving drug safety.1 To test if this supposition holds for prodrug design, dose escalation studies were performed with the chemically robust derivative 8 in Swiss Webster mice. Mice tolerated this analogue without showing signs of toxicity and weight loss when injected intraperitoneally (i.p.) once a day for five consecutive days (qd×5) at a dose of 1.6 mg/kg. For comparison, compound 1' was significantly more toxic and showed an MTD of 0.1 mg/kg when the same dosing schedule was applied.

Thus, in one embodiment of the present invention, a versatile platform for tuning the pharmacological parameters of potent platinum-acridines has been discovered. The invention demonstrates that the metal-based pharmacophore is compatible with the classical concept of enzymatic prodrug activation. These features are likely to translate into more favorable ADME and improved safety.

EXPERIMENTAL

Materials, General Procedures, and Instrumentation. All reagents were used as obtained from commercial sources without further purification unless indicated otherwise. Compound 1'[5] (chloride salt) and N-(acridin-9-yl)-N'-methylethane-1,2-diamine (13) were prepared according to published procedures. The platinum-nitrile precursors (12a-g) were synthesized from the corresponding nitrites (11a-d) and silver-ion activated diam(m)inedichloroplatmum(II) complexes.

$^1$H NMR spectra of the target compounds and intermediates were recorded on Bruker Advance DRX-500 and 300 MHz instruments. Proton-decoupled $^{13}$C NMR spectra were recorded on a Bruker DRX-500 instrument operating at 125.8 MHz. 2-D $^1$H-$^{13}$C gradient-selected Heteronuclear Multiple Bond Coherence (gsHMBC) experiments and temperature-dependent spectra were acquired on a Bruker DRX-500 instrument equipped with a TBI probe and a variable-temperature unit. 2-D HMBC spectra were collected with 2048 pts in $t_2$ (sw=6510 Hz), 256 pts in $t_1$ (sw=27670 Hz), 128 scans per $t_1$ increment, and a recycle delay (d1) of 1.5 s. Chemical shifts ($\delta$) are given in parts per million (ppm) relative to internal standard tetramethylsilane (TMS). $^1$H NMR data is reported in the conventional form including chemical shift ($\delta$, ppm), multiplicity (s=singlet, d=doublet, t=triplet, q=quartet, m=multiplet, br=broad), coupling constants (Hz), and signal integrations. $^{13}$C NMR data are reported as chemical shift listings ($\delta$, ppm). The NMR spectra were processed and analyzed using the MestReNova software package.

HPLC-grade solvents were used for all HPLC and mass spectrometry experiments. LC-ESMS analysis was performed on an Agilent 1100LC/MSD ion trap mass spectrometer equipped with an atmospheric pressure electrospray ionization source. Eluent nebulization was achieved with a $N_2$ pressure of 50 psi and solvent evaporation was assisted by a flow of $N_2$ drying gas (350° C.). Positive-ion mass spectra were recorded with a capillary voltage of 2800 V and a mass-to-charge scan range of 150 to 2200 m/z. To establish the purity of target compounds, samples were diluted in methanol containing 0.1% formic acid and separated using a 4.6 mm×150 mm reverse-phase Agilent ZORBAX SB-C18 (5 μm) analytical column at 25° C., by using the following solvent system: solvent A, optima water, and solvent B, methanol/0.1% formic acid, with a flow rate of 0.5 mL/min and a gradient of 95% A to 5% A over 30 minutes. HPLC traces were recorded with a monitoring wavelength range of 363-463 nm. Peak integration was done using the LC/MSD Trap Control 4.0 data analysis software. Analytical purity of greater than 95% was confirmed this way for all target compounds prior to analytical and biological experiments.

Synthesis of $[PtCl(en)C_{22}H_{27}N_4O_2](NO_3)_2$ (2). Precursor complex 12a (240 mg, 0.5 mmol) was dissolved in 10 mL of anhydrous DMF and the solution was cooled to −20° C. Acridine-amine 13 (138 mg, 0.55 mmol) was added to the solution, and the suspension was stirred at 4° C. for 24 h. The reaction mixture was added dropwise into 200 mL of anhydrous ethyl ether, and the resulting yellow slurry was vigorously stirred for 30 min. The precipitate was recovered by membrane filtration, dried in a vacuum overnight, and dissolved in 20 mL of methanol containing 1 equivalent of $HNO_3$. After removal of the solvent by rotary evaporation, the crude product was recrystallized from hot ethanol, affording 2 as a 3:1 mixture of E and Z isomers. Yield: 238 mg (71%). $^1$H NMR (300 MHz, MeOH-$d_4$) $\delta$ 8.61-8.51 (m, 2H), 8.13-7.75 (m, 4H), 7.75-7.45 (m, 2H), 6.57-6.87 (m, 1H), 5.50 (s, 1.5H, E-isomer), 5.49-5.39 (m, 4H), 4.76 (s, 0.5H, Z-isomer), 4.59 (m, 0.5H, Z-isomer), 4.45 (t, J=6.3 Hz, 1.5H, E-isomer), 4.02 (t, J=6.3 Hz, 1.5H, E-isomer), 3.56-3.39 (m, 0.5H, Z-isomer), 3.14 (s, 2.25H, E-isomer), 2.61-2.57 (m, 4H), 2.38-2.06 (m, 2H), 1.76-1.40 (m, 2H), 1.02-0.75 (m, 3H). $^{13}$C NMR (75 MHz, MeOH-$d_4$) $\delta$ 172.50, 171.76, 165.14, 163.38, 158.48, 139.87, 135.21, 124.99, 124.02, 118.28, 112.63, 63.55, 61.87, 35.03, 17.69, 12.43. MS (ESI, positive-ion mode): m/z for $C_{24}H_{35}ClN_6O_2Pt$ ([M]$^+$), 669.22; found, 669.3.

Synthesis of $[PtCl(en)C_{26}H_{35}N_4O_2](NO_3)_2$ (3). Compound 3 was prepared according to the procedure described for 2 from precursor 12b with a yield of 69%. $^1$H NMR (300 MHz, MeOH-$d_4$) $\delta$ 8.82-8.40 (m, 2H), 8.11-7.78 (m, 4H), 7.77-7.50 (m, 2H), 5.52 (s, 1.5H, E-isomer), 5.42-5.13 (m, 4H), 4.64-4.54 (m, 0.5H, Z-isomer), 4.48 (t, J=6.5 Hz, 1.5H, E-isomer), 4.03 (t, J=6.4 Hz, 2H, E-isomer), 3.15 (s, 3H), 2.75-2.47 (m, 4H), 2.44-2.11 (m, 1H), 1.54-1.13 (m, 8H), 0.97-0.71 (m, 6H). $^{13}$C NMR (75 MHZ, MeOH-$d_4$) $\delta$ 176.65, 176.01, 167.30, 164.85, 159.90, 141.38, 136.77, 126.49, 125.61, 119.88, 114.12, 66.90, 65.27, 49.87, 48.16, 35.48, 21.58, 15.45, 14.31. MS (ESI, positive-ion mode): m/z for $C_{28}H_{43}ClN_6O_2Pt$ ([M-H]$^+$), 724.28; found, 724.4.

Synthesis of $[PtCl(NH_3)_2C_{26}H_{35}N_4O_2](NO_3)_2$ (4). Compound 4 was prepared according to the procedure described for 2 from precursor 12c with a yield of 74%. $^1$H NMR (300

MHz, MeOH-d$_4$) δ 8.56 (d, J=8.7, 2H), 8.03 (ddt, J=9.2, 5.8, 1.8 Hz, 2H), 7.95-7.79 (m, 2H), 7.75-7.51 (m, 2H), 5.56 (s, 1.5H, E-isomer), 4.67-4.54 (s, 0.5H, Z-isomer), 4.48 (t, J=6.5 Hz, 1.5H, E-isomer), 4.18 (bs, 3H), 4.02 (t, J=6.5 Hz, 1.5H), 3.93 (bs, 3H), 3.14 (s, 3H), 2.36-2.16 (m, 1H), 1.56-1.03 (m, 8H), 0.90-0.68 (m, 6H). $^{13}$C NMR (75 MHz, MeOH-d$_4$) δ176.67, 176.07, 164.74, 159.89, 141.39, 136.76, 136.76, 126.77, 125.60, 119.88, 114.20, 65.32, 46.33, 46.14, 35.49, 21.58, 14.29. MS (ESI, positive-ion mode): m/z for C$_{26}$H$_{41}$ClN$_6$O$_2$Pt ([M]$^+$), 699.26; found, 699.3.

Synthesis of [PtCl(pn)C$_{26}$H$_{35}$N$_4$O$_2$](NO$_3$)$_2$ (5). Compound 5 was prepared according to the procedure described for 2 from precursor 12d with the yield of 77%. $^1$H NMR (300 MHz, MeOH-d$_4$) δ 8.61 (dd, J=20.8, 8.5 Hz, 2H), 8.14-7.95 (m, 2H), 7.87 (dd, J=9.0, 4.2 Hz, 2H), 7.75-7.53 (m, 2H), 6.83-6-73 (m, 1H), 5.53 (s, 1.5H, E-isomer), 5.29-4.88 (m, 4H), 4.68-4.58 (m, 0.5H, Z-isomer), 4.55 (t, J=6.6 Hz, 1.5H, E-isomer), 4.03 (t, J=6.4 Hz, 1.5H, E-isomer), 3.68-3.44 (m, 0.5H, Z-isomer), 3.15 (s, 2H), 2.95-2.52 (m, 4H), 2.41-2.07 (m, 1H), 1.92-1.69 (m, 2H), 1.59-0.98 (m, 8H), 0.98-0.64 (m, 6H). $^{13}$C NMR (75 MHz, MeOH-d$_4$) δ 176.68, 176.22, 164.89, 159.90, 141.41, 136.76, 126.56, 125.60, 119.88, 119.88, 113.48, 49.86, 46.29, 44.42, 43.63, 43.55, 35.54, 29.39, 21.60, 14.31. MS (ESI, positive-ion mode): m/z for C$_{29}$H$_{45}$ClN$_6$O$_2$Pt ([M]$^+$), 739.29; found, 739.4.

Synthesis of [PtCl(en)C$_{28}$H$_{39}$N$_4$O$_2$](NO$_3$)$_2$ (6). Compound 6 was prepared according to the procedure described for 2 from precursor 12e with the yield of 83%. $^1$H NMR (300 MHz, MeOH-d$_4$) δ 8.46 (dd, J=20.8, 8.5 Hz, 2H), 7.91 (m, 2H), 7.77 (dd, J=9.0, 4.2 Hz, 2H), 7.54 (m, 2H), 6.08 (s, 1H), 5.36-5.11 (m, 4H), 4.33 (t, J=6.6 Hz, 2H), 4.03 (t, J=6.4 Hz, 2H), 3.88 (m, 2H), 3.03 (s, 3H), 2.97 (m, 2H), 2.55-2.37 (m, 4H), 2.10-2.03 (m, 3H), 1.59-0.98 (m, 8H), 0.98-0.64 (m, 6H). $^{13}$C NMR (75 MHz, MeOH-d$_4$) δ178.08, 170.02, 159.98, 141.37, 136.71, 126.52, 125.53, 119.85, 114.10, 64.83, 46.53, 35.81, 29.39, 27.15, 21.67, 14.34. MS (ESI, positive-ion mode): m/z for C$_{30}$H$_{47}$ClN$_6$O$_2$Pt ([M]$^+$), 752.31; found, 752.4.

Synthesis of [PtCl(en)C$_{24}$H$_{31}$N$_4$O$_2$](NO$_3$)$_2$ (7). Compound 7 was prepared according to the procedure described for 2 from precursor 12f with the yield of 89%. $^1$H NMR (300 MHz, MeOH-d$_4$) δ 8.72-8.46 (m, 2H), 8.01 (ddd, J=8.1, 6.9, 1.0 Hz, 3H), 7.92-7.80 (m, 3H), 7.64 (ddd, J=8.3, 6.9, 1.2 Hz, 2H), 6.16 (s, 1H), 5.44-5.22 (m, 4H), 4.42 (t, J=6.5 Hz, 2H), 4.18 (t, J=6.5 Hz, 2H), 3.98 (t, J=6.5 Hz, 2H), 3.12-3.02 (m, 5H), 2.74-2.46 (m, 4H), 2.34-1.99 (m, 4H), 1.58 (d, J=7.3 Hz, 2H), 0.90 (t, J=7.4 Hz, 3H). $^{13}$C NMR (75 MHz, MeOH-d$_4$) δ 175.33, 170.11, 160.04, 141.38, 136.69, 126.43, 125,50, 119.87, 114.12, 64.7, 36.84, 32.07, 27.10, 19.37, 13.94. MS (ESI, positive-ion mode): m/z for C$_{26}$H$_{39}$ClN$_6$O$_2$Pt ([M]$^+$), 697.25; found, 697.3.

Synthesis of [PtCl(pn)C$_{28}$H$_{39}$N$_4$O$_2$](NO$_3$)$_2$ (8). Complex 8 was prepared according to the procedure described for 2 from precursor 12g with the yield of 76%. $^1$H NMR (300 MHz, MeOH-d$_4$) δ 8.54 (d, J=8.6 Hz, 2H), 8.10-7.76 (m, 4H), 7.59 (t, J=7.4 Hz, 2H), 4.40 (t, J=6.1 Hz, 2H), 4.17 (t, J=6.2 Hz, 3H), 3.97 (t, J=6.0 Hz, 3H), 3.21-2.98 (m, 5H), 2.94-2.54 (m, 4H), 2.40-1.95 (m, 3H), 1.79 (s, 2H), 1.56-0.99 (m, 8H), 0.92-0.68 (m, 6H). $^{13}$C NMR (75 MHz, MeOH-d$_4$) δ 178.02, 169.87, 159.85, 141.33, 136.67, 126.61, 125.50, 119.87, 114.13, 64.86, 46.56, 44.31, 43.63, 35.83, 29.29, 26.76, 21.69, 14.37. MS (ESI, positive-ion mode): m/z fox C$_{31}$H$_{49}$ClN$_6$O$_2$Pt ([M]$^+$), 767.33; found, 767.4.

The following acronyms are used for the various reagents: DMF: Dimethylformamide; DCM: Dichloromethane; MeOH: Methanol; TEA: Triethylamine; and TFA: Trifluoroacetic acid.

Scheme S.1 shows the general synthetic scheme for how the various intermediates were made.

Scheme S.1. General synthetic scheme for the preparation of precursors S1-S4

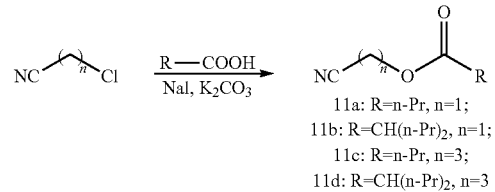

11a: R=n-Pr, n=1;
11b: R=CH(n-Pr)$_2$, n=1;
11c: R=n-Pr, n=3;
11d: R=CH(n-Pr)$_2$, n=3

Synthesis of 11a. To a mixture of butyric acid (10.6 g, 0.12 mol), anhydrous potassium carbonate (20.7 g, 0.15 mol) and sodium iodide (22.5 g, 0.15 mol) in 80 ml of acetonitrile was added 2-chloroacetonitrile (7.5 g, 0.1 mol) in 5 ml acetonitrile at room temperature. When the addition was complete, the mixture was refluxed for 16 h. The acetonitrile was then removed by rotary evaporation and the residue was redissolved in 100 ml CH$_2$Cl$_2$ and washed with 10% aqueous K$_2$CO$_3$ and brine. The organic layers were collected, dried over MgSO$_4$, and concentrated. This crude material was dried in a vacuum at 45° C. overnight to remove unreacted 2-chloroacetonitrile, affording 11.2 g of 11a as a colorless oil (yield: 88%). $^1$H NMR (300 MHz, CDCl$_3$) δ 4.73 (s), 2.40 (t, J=7.3 Hz, 2H), 1.68 (h, J=7.6 Hz, 3H), 0.98 (t, J=7.4 Hz, 2H). $^{13}$C NMR (75 MHz, CDCl$_3$) δ 171.94, 114.58, 48.12, 35.22, 18.09, 13.46.

Synthesis of 11b. Compound 11b was prepared according to the procedure described for 11a, by using 4-chlorobutanenitrile as the precursor with a yield of 74%. $^1$H NMR (300 MHz, Chloroform-d) δ 4.19 (t, J=6.0 Hz, 2H), 2.47 (t, J=7.2 Hz, 2H), 2.31 (t, J=7.4 Hz, 2H), 2.01 (h, J=7.0, 5.8 Hz, 2H), 1.66 (h, J=7.4 Hz, 2H), 0.96 (t, J=7.4 Hz, 3H). $^{13}$C NMR (75 MHz, CDCl$_3$) δ 173.27, 118.90, 61.86, 35.89, 24.80, 18.28, 14.21, 13.58.

Synthesis of 11c. Compound 11c was prepared according to the procedure described for 11a, by using valproic acid as the precursor with a yield of 84%. $^1$H NMR (300 MHz, Chloroform-d) δ 4.67 (s, 2H), 2.43 (m, 1H), 1.48 (m, 4H), 1.24 (m, 4H), 0.85 (t, J=7.3 Hz, 6H). $^{13}$C NMR (75 MHz, CDCl$_3$) δ 174.84, 114.55, 47.96, 44.69, 34.32, 20.49, 13.84, 0.96.

Synthesis of 11d. Compound 11d was prepared according to the procedure described for 11a, by using 4-chlorobutanenitrile and valproic acid as the precursors with a yield of 69%. $^1$H NMR (300 MHz, Chloroform-d) δ 4.09 (t, J=6.0 Hz, 2H), 2.37 (t, J=6.1 Hz, 2H), 2.30 (m, 1H), 1.92 (m, 2H), 1.40 (m, 4H), 1.18 (m, 4H), 0.81 (m, 6H). $^{13}$C NMR (75 MHz, CDCl$_3$) δ 176.10, 118.77, 61.66, 45.09, 34.50, 24.84,, 20.56, 14.13, 13.88.

Scheme S.2. Chemical structures of precursors 12a-12g.

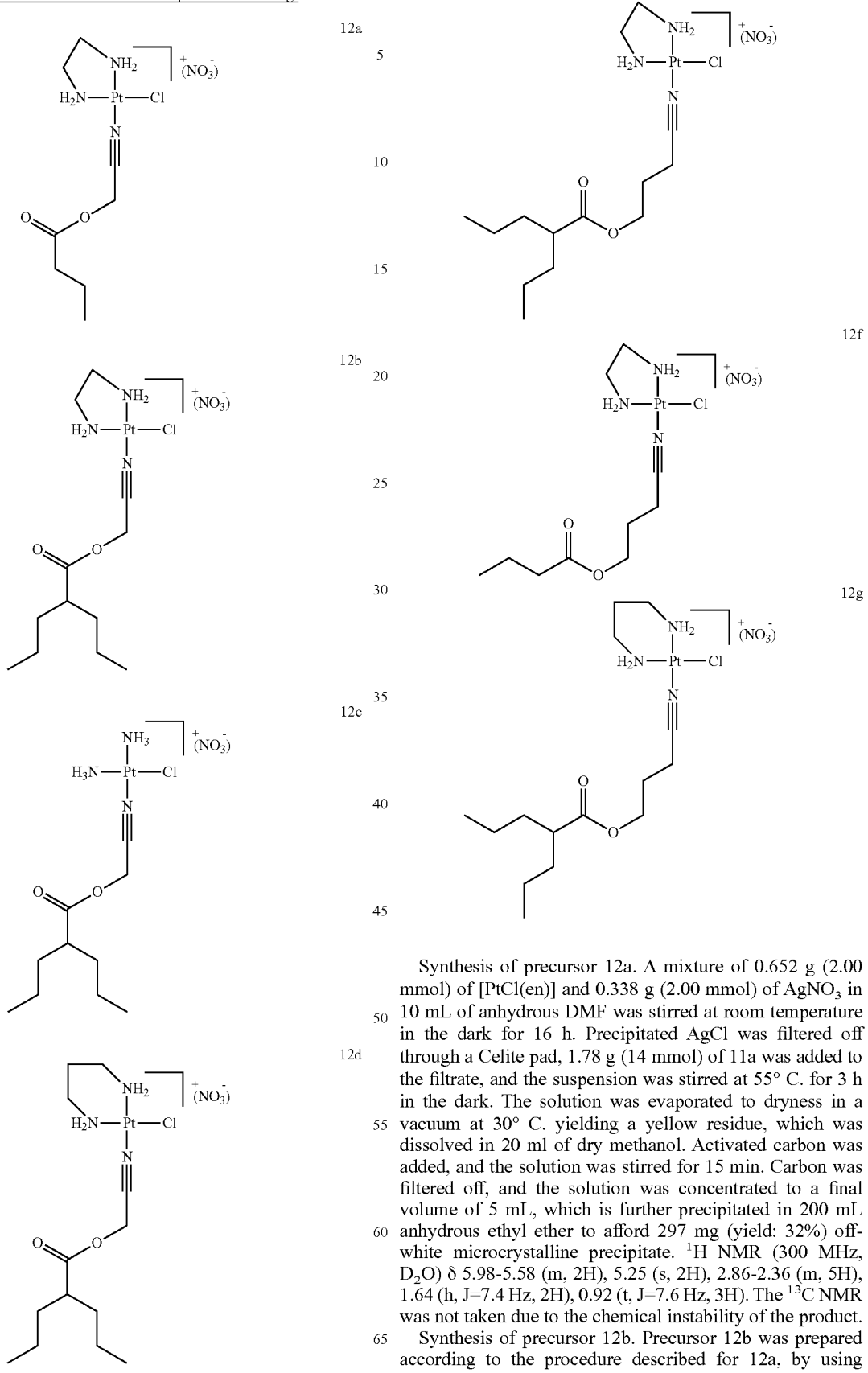

Synthesis of precursor 12a. A mixture of 0.652 g (2.00 mmol) of [PtCl(en)] and 0.338 g (2.00 mmol) of AgNO$_3$ in 10 mL of anhydrous DMF was stirred at room temperature in the dark for 16 h. Precipitated AgCl was filtered off through a Celite pad, 1.78 g (14 mmol) of 11a was added to the filtrate, and the suspension was stirred at 55° C. for 3 h in the dark. The solution was evaporated to dryness in a vacuum at 30° C. yielding a yellow residue, which was dissolved in 20 ml of dry methanol. Activated carbon was added, and the solution was stirred for 15 min. Carbon was filtered off, and the solution was concentrated to a final volume of 5 mL, which is further precipitated in 200 mL anhydrous ethyl ether to afford 297 mg (yield: 32%) off-white microcrystalline precipitate. $^1$H NMR (300 MHz, D$_2$O) δ 5.98-5.58 (m, 2H), 5.25 (s, 2H), 2.86-2.36 (m, 5H), 1.64 (h, J=7.4 Hz, 2H), 0.92 (t, J=7.6 Hz, 3H). The $^{13}$C NMR was not taken due to the chemical instability of the product.

Synthesis of precursor 12b. Precursor 12b was prepared according to the procedure described for 12a, by using [PtCl$_2$(en)] and 11b as the precursors with a yield of 37%.

¹H NMR (300 MHz, D₂O) δ 5.95-5.43 (m, 2H), 5.22 (s, 1H), 2.79-2.42 (m, 5H), 1.65-1.39 (m, 4H), 1.23 (h, J=7.5 Hz, 4H), 0.83 (t, J=7.3 Hz, 6H).

Synthesis of precursor 12c. Precursor 12c was prepared according to the procedure described for 12a, by using [(NH₃)₂PtCl₂] and 11b as the precursors with a yield of 29%. ¹H NMR (300 MHz, Methanol-d4) δ 4.77 (s, 2H), 2.46-2.35 (m, 1H), 1.62-1.33 (m, 4H), 1.32-1.13 (m, 4H), 0.82 (t, J=7.3 Hz, 6H).

Synthesis of precursor 12d. Precursor 12d was prepared according to the procedure described for 12a, by using [PtCl₂(Pn)] and 11b as the precursors with a yield of 39%. ¹H NMR (300 MHz, Methanol-d4) δ 5.95-5.43 (m, 2H), 5.22 (s, 1H), 2.83-2.38 (m, 5H), 1.78-1.66 (m, 2H), 1.65-1.39 (m, 4H), 1.23 (h, J=7.5 Hz, 4H), 0.83 (t, J=7.3 Hz, 6H).

Synthesis of precursor 12e. Precursor 12e was prepared according to the procedure described for 12a, by using [PtCl₂(en)] and 11d as the precursors with a yield of 84%. ¹H NMR (300 MHz, Methanol-$d_4$) δ 4.21 (t, J=6.1 Hz, 2H), 3.08 (t, J=7.1 Hz, 1H), 2.69-2.41 (m, 5H), 2.19-2.03 (m, 2H), 1.72-1.39 (m, 4H), 1.42-1.24 (m, 4H), 0.94 (t, J=7.2 Hz, 6H).

Synthesis of precursor 12f. Precursor 12f was prepared according to the procedure described for 12a, by using [PtCl₂(en)] and 11c as the precursors with a yield of 86%. ¹H NMR (300 MHz, Methanol-d4) δ 4.21 (t, J=6.0 Hz, 2H), 3.08 (t, J=7.0 Hz, 2H), 2.82-2.48 (m, 2H), 2.42 (t, J=7.4 Hz, 2H), 2.19-1.99 (m, 2H), 1.68 (h, J=7.4 Hz, 2H), 0.98 (t, J=7.4 Hz, 3H).

Synthesis of precursor 12g. Precursor 12g was prepared according to the procedure described for 12a, by using [PtCl₂(pn)] and 11d as the precursors with a yield of 84%. ¹H NMR (300 MHz, Methanol-d4) δ 4.76-3.94 (m, 2H), 3.00-2.87 (m, 2H), 2.81-2.27 (m, 5H), 2.00 (p, J=6.9 Hz, 2H), 1.73 (p, J=5.4 Hz, 3H), 1.62-1.28 (m, 4H), 1.29-1.16 (m, 4H), 0.83 (t, J=7.2 Hz, 8H).

Synthesis of compound 1'''. Compound 1''' was prepared according to the procedure reported previously [1]. ¹H NMR (300 MHz, DMF-d₇) δ 13.89 (s, 1H), 9.89 (s, 1H), 8.77-8.67 (m, 2H), 8.19-7.91 (m, 4H), 7.66-7.59 (m, 2H), 6.19 (s, 1H), 5.35-4.98 (m, 4H), 4.51 (t, J=5.7 Hz, 2H), 4.12 (t, J=6.5 Hz, 2H), 3.48-3.37 (m, 4H), 3.19 (s, 3H), 2.69 (s, 3H), 1.83 (brs, 2H). ¹³C NMR (75 MHz, DMF-d₇) δ 166.57, 159.26, 140.81, 135.92, 126.48, 124.52, 119.60, 113.67, 65.87, 47.62, 43.95, 43.32, 28.59, 22.33, 15.50.

Time-Dependent NMR Spectroscopy. NMR spectra in arrayed experiments were collected at 37° C. on a Bruker 500 DRX spectrometer equipped with a triple-resonance broadband inverse probe and a variable temperature unit. Reactions were performed with 2 mM platinum complex dissolved in either 600 μL of 10 mM phosphate buffer (PB, D₂O, pH*=7.0) or in 600 μL of phosphate-buffered saline (1×PBS, D₂O, pH*=7.0). The 1-D ¹H kinetics experiments were carried out as a standard Bruker arrayed 2-D experiment using a variable-delay list. Each incremented 1-D spectrum was processed using the same procedure, and suitable signals of the ester moiety were integrated. Data were processed with MestReNova NMR software. The concentrations of platinum complex at each time point were deduced from relative peak intensities, averaged over multiple signals to account for differences in proton relaxation, and fitted to a first-order exponential decay function in Origin 8.0 (OriginLab, Northampton, Mass.).

Chemical Hydrolysis Assay. The ester hydrolysis study of compounds 2-8 was carried out by incubating 1 mM of each test compound in 10 mM phosphate buffer (pH 7.4) or 1×PBS containing ~150 mM NaCl at 37° C. At various time points samples were withdrawn from the reaction mixture and analyzed by in-line LC-ESMS. Chromatographic separations were performed with a 4.6 mm×150 mm reverse-phase Agilent ZORBAX SB-C18 (5 μm) analytical column with the column temperature maintained at 25° C. The following solvent system was used: solvent A, optima water, and solvent B, methanol/0.1% formic acid, at a flow rate of 0.5 mL/min and a gradient of 95% A to 5% A over 15 min.

Enzymatic Cleavage Assay. To study ester cleavage in compounds 2-8 by recombinant human carboxylesterase-2 (rhCES-2), 30 μM of each compound was incubated with 400 μg/mL hCES-2 (BD Biosciences, San Jose, Calif., USA) at 37° C. in 1×PBS. Aliquots were withdrawn at various time points, quenched in an equal volume of methanol, and centrifuged for 5 min at 10000 g to denature and precipitate protein. The supernatant was collected and subjected to product separation and analysis using in-line LC-ESMS. Chromatography was performed on a 4.6 mm×150 mm reverse-phase Agilent ZORBAX SB-C18 (5 μm) analytical column with the column temperature maintained at 25° C. The following solvent system was used: solvent A, optima water, and solvent B, methanol/0.1% formic acid, at a flow rate of 0.5 mL/min and a gradient of 95% A to 5% A over 15 min.

Determination of Partition Coefficients (log D). To obtain octanol-saturated water and water-saturated octanol, 100 mL of PBS was stirred with 100 mL of octanol for 24 h, followed by centrifugation for 5 min. The platinum complexes were dissolved in 1.0 mL of octanol-saturated PBS to a typical concentration of 0.1 mM and then mixed with 1.0 mL water-saturated octanol. Triplicates of each experiment were mixed in a multi-tube vortexer incubator for 16 h at room temperature and then centrifuged for 5 min. The layers were separated carefully, and the content of platinum-acridines was determined spectrophotometrically at 413 nm (with $\epsilon_{413}$=10,000 M⁻¹ cm⁻¹ in octanol-saturated PBS and $\epsilon_{413}$=8,600 M⁻¹ cm⁻¹ in PBS-saturated octanol). The partition coefficients (D) of the samples were then determined as the quotient of the concentration of compound in octanol and the concentration in the aqueous layer. Reported log D values are the mean±standard deviations of three determinations.

Cell Culture Maintenance. The human non-small cell lung cancer cell lines, NCI-H1435 and A549 (adenocarcinomas) were obtained from the American Type Culture Collection (Rockville, Md., USA). A549 cells were cultured in HAM's F12K media (Gibco) supplemented with 10% fetal bovine serum (FBS), 10% penstrep (P&S), 10% L-glutamine, and 1.5 g/L NaHCO₃. NCI-H1435 cells were cultured in serum-free 1:1 DMEM/F12 media (Gibco) containing 2.436 g/L NaHCO₃, 0.02 mg/mL insulin, 0.01 mg/mL transferrin, 25 nM sodium selenite, 50 nM hydrocortisone, 1 ng/mL epidermal growth factor, 0.01 mM ethanolamine, 0.01 mM phosphorylethanolamine, 100 pM triiodothyronine, 0.5% (w/v) bovine serum albumin (BSA), 10 mM HEPES, 0.5 mM sodium pyruvate, and an extra 2 mM L-glutumine (final concentration 4.5 mM). Cells were incubated at a constant temperature at 37° C. in a humidified atmosphere containing 5% CO₂ and were subcultured every 2-3 days in order to maintain cells in logarithmic growth, except for slowly proliferating NCI-H1435, which was subcultured every 7 days.

Cytotoxicity Assay. The cytotoxicity studies were carried out according to a standard protocol using the Celltiter 96 aqueous nonradioactive cell proliferation assay kit (Promega, Madison, Wis.). Stock solutions (5-10 mM) of 1'-8 were made in DMF and serially diluted with media prior to incubation with cancer cells. All drugs and controls were tested at the indicated concentrations in triplicate wells on duplicate plates. Incubations were carried out for 72 h and cell viabilities were determined by comparing drug-treated wells with control cells.

Synthesis of Conjugates on a Microscale for Library Assembly (Note: This procedure is used for prescreening purposes and can be scaled up to preparation of batches for animal studies and clinical applications).

Stock solutions of the carboxylic acid-modified platinum-(benz)acridines (10 mM), coupling reagent PyBOP (10 mM), amines to be linked via amide bond formation (10 mM), and Hünig's base (10 mM) are prepared in anhydrous DMF. Coupling reactions are carried out in 1.5-mL Eppendorf tubes by mixing all the reaction components using the following volumes: platinum-acridine (10 µL), PyBOP (12 µL), Hünig's base (10 µL), and selected amines (15 µL). The reaction mixtures are incubated at room temperature for 16 hours. To quench the reactions, 1 mL of diethyl ether is added to precipitate platinum complexes, which are collected by centrifugation, washed with 0.5 mL of dichloromethane, and redisolved in 20 µL of phosphate-buffered saline (PBS) (pH 7.4). Traces of unreacted precursors and byproducts are soluble in diethyl ether, or dichloromethane, and can be removed by washing the solid and discarding the supernatant. To characterize conjugates and to determine conversion yields, 5-µL samples are removed from the PBS solutions and diluted with 400 µL of methanol containing 0.1% formic acid prior to LC-ESMS analysis. Chromatographic separations are performed with a 4.6 mm×150 mm reverse-phase Agilent ZORBAX SB-C18 (5 µm) analytical column with the column temperature maintained at 25° C. The binary mobile phase consisted of: solvent A, optima water, and solvent B, methanol/0.1% formic acid delivered at a gradient of 95% A to 5% A over 30 minutes and a flow rate of 0.5 mL/min. The formation and the extent of conversion of the platinum-acridines was monitored in the corresponding chromatograms using the LC/MSD Trap Control 4.0 data analysis software.

Other coupling agents that may be used in an embodiment of the invention include
CDI: 1,1'-Carbonyldiimidazole
EDC: 1-Ethyl-3-(3-dimethylaminopropyl)carbodiimide
HATU: (1-[Bis(dimethylamino)methylene]-1H-1,2,3-triazolo[4,5-b]pyridinium-3-oxid hexafluorophosphate)
HBTU: N,N,N',N'-Tetramethyl-O-(1H-benzotriazol-1-yl) uronium hexafluorophosphate
COMU: (1-Cyano-2-ethoxy-2-oxoethylidenaminooxy)dimethylamino-morpholino-carbenium hexafluorophosphate
PyBOP: (Benzotriazol-1-yloxy)tripyrrolidinophosphonium hexafluorophosphate
TSTU: O-(N-Succinimidyl)-N,N,N',N'-tetramethyluronium tetrafluoroborate Presereening of the Library in Cancer Cell Lines Reaction mixtures can be tested directly in human cancer cell lines to evaluate their anticancer activity. Briefly, cells are preincubated at 37° C. overnight and then treated with an appropriate concentration (e.g., 200 nM) of the conjugates from the reaction mixtures (the concentrations of the mixtures can be readily assessed spectrophotometrically ($\lambda_{max}$=413 nm, $\epsilon$=10,000 $M^{-1}$ $cm^{-1}$)) and the corresponding precursor modules as controls. After an incubation period of 72 h, 20 µL of MTS/PMS solution (or MTT, depending on the cell proliferation kit used) is added to each well and incubated at 37° C. for 4 h. The absorbance of tetrazolium dye is measured at 490 nm using a plate reader. The fraction of viable cells is calculated as a percentage of untreated control and is reported as the mean±standard deviation for 3 incubations of each compound. $IC_{50}$ values are calculated from non-linear curve fits using a sigmoidal dose-response equation in GraphPad Prism (GraphPad Software, La Jolla, Calif.) and are averages of two individual experiments performed in triplicate.

In an embodiment, the present invention relates to:

Synthesis of (extended) carboxylic ester-modified platinum-(benz)acridine agents for generating ester-, amide-, and carbamate-based conjugates with other functional entities. Modules include, but are not limited to: protecting groups, lipophilic modifiers, micelle-forming molecules and lipids, molecularly targeted therapies, hormone therapies, chemosensitizers, peptides;

Conjugation reactions that can be performed with common coupling reagents (see list given above), are compatible with platinum, produce high-yields under mild conditions without side products; and are amenable to modular-library assembly and high-throughput screening.

Ester linkages can be designed to be sufficiently stable in circulation and resist cleavage by human esterases (e.g., hCES-2), which allows delivery of the intact conjugates to the tumor site, but undergo accelerated hydrolysis once internalized into cancer cells.

Multiple agents can be co-delivered in form of conjugates for optimal cellular uptake and subcellular localization.

Safer delivery of cytotoxic payload, improved pharmacokinetics Safer delivery of cytotoxic payload, improved pharmacokinetics It should be understood that it is contemplated and therefore within the scope of the invention that any feature that is associated with the compounds, compositions and methods of the present invention can be combined with any other feature even if those features are not discussed together. When a range is given, it is contemplated that all integral numbers that fall within that range are contemplated as end-points for a new sub-range. It is also contemplated that when a Markush group or if alternative embodiments are enumerated, it is contemplated and therefore within the scope of the invention that any of the members of that Markush group or any of the alternative embodiments can be disclaimed. Finally, minor modifications are contemplated that do not depart from the spirit and scope of the present invention.

The following references are incorporated by reference in their entireties.

1. Huttunen, K. M.; Raunio, H.; Rautio, J. Prodrugs-from serendipity to rational design. *Pharmacol. Rev.* 2011, 63, 750-771.
2. Lammers, T.; Kiessling, F.; Hennink, W. E.; Storm, G. Drug targeting to tumors: principles, pitfalls and (pre-) clinical progress. *J. Control. Release* 2012, 161, 175-187.
3. Kerns, E. H.; Di, L. Pharmaceutical profiling in drug discovery. *Drug Discov. Today* 2003, 8, 316-323.
4. Suryudi, J.; Bierbach, U. DNA metalating-intercalating hybrid agents for the treatment of chemoresistant cancers. *Chem. Eur. J.* 2012, 18, 12926-12934.
5. Ma, Z.; Choudhury, J. R.; Wright, M. W.; Day, C. S.; Saluta, G.; Kucera, G. L.; Bierbach, U. A non-cross-linking platinum-acridine agent with potent activity in non-small-cell lung cancer. *J. Med. Chem.* 2008, 51, 7574-7580.
6. Cheung-Ong, K.; Song, K. T.; Ma, Z.; Shabtai, D.; Lee, A. Y.; Gallo, D.; Heisler, L. E.; Brown, G. W.; Bierbach, U.; Giaever, G.; Nislow, C. Comparative chemogenomics to examine the mechanism of action of dna-targeted platinum-acridine anticancer agents. *ACS Chem. Biol.* 2012, 7, 1892-1901.
7. Qiao, X.; Zeitany, A. E.; Wright, M. W.; Essader, A. S.; Levine, K. E.; Kucera, G. L.; Bierbach, U. Analysis of the DNA damage produced by a platinum-acridine antitumor agent and its effects in NCI-H460 lung cancer cells. *Metallomics* 2012, 4, 645-652.
8. Smyre, C. L.; Saluta, G.; Kute, T. E.; Kucera, G. L.; Bierbach, U. Inhibition of DNA Synthesis by a Platinum-Acridine Hybrid Agent Leads to Potent Cell Kill in Non-Small Cell Lung Cancer. *ACS Med. Chem. Lett.* 2011, 2, 870-874.
9. Ma, Z.; Rao, L.; Bierbach, U. Replacement of a thiourea-S with an amidine-NH donor group in a platinum-acridine antitumor compound reduces the metal's reactivity with cysteine sulfur. *J. Med. Chem.* 2009, 52, 3424-3427.
10. Lullmann, H.; Mohr, K.; Ziegler, A.; Bieger, D. *Color Atlas of Pharmacology.* 2nd ed.; Thieme Medical Publishers: Stuttgart, Germany 2000, pp. 32-43.
11. Pratt, S. E.; Durland-Busbice, S.; Shepard, R. L.; Heinz-Taheny, K.; Iversen, P. W.; Dantzig, A. H. Human carboxylesterase-2 hydrolyzes the prodrug of gemcitabine (LY2334737) and confers prodrug sensitivity to cancer cells. *Clin. Cancer Res.* 2013, 19, 1159-1168.
12. Graham, L. A.; Suryadi, J.; West, T. K.; Kucera, G. L.; Bierbach, U. Synthesis, aqueous reactivity, and biological evaluation of carboxylic Acid ester-functionalized platinum-acridine hybrid anticancer agents. *J. Med. Chem.* 2012, 55, 7817-7827.
13. Imai, T.; Taketani, M.; Shii, M.; Hosokawa, M.; Chiba, K. Substrate specificity of carboxylesterase isozymes and their contribution to hydrolase activity in human liver and small intestine. *Drug Metab. Dispos.* 2006, 34, 1734-1741.
14. Ding, S.; Qiao, X.; Kucera, G. L.; Bierbach, U. Using a build-and-click approach for producing structural and functional diversity in DNA-targeted hybrid anticancer agents. *J. Med. Chem.* 2012, 55, 10198-10203.
15. Natile, G.; Intini, F. P.; Bertani, R.; Michelin, R. A.; Mozzon, M.; Sbovata, S. M.; Venzo, A.; Seraglia, R. Synthesis and characterisation of the amidine complexes trans-[PtCl(NH$_3$)-{HN=(NH$_2$)R}$_2$]Cl (R=Me, Ph, CH$_2$Ph) derived from addition of NH$_3$ to the coordinated nitrites in trans-[PtCl$_2$(NCR)$_2$]. *J. Organomet. Chem.* 2005, 690, 2121-2127.
16. Michelin, R. A.; Sgarbossa, P.; Sbovata, S. M.; Gandin, V.; Marzano, C.; Bertani, R. Chemistry and biological activity of platinum amidine complexes. *ChemMedChem* 2011, 6, 1172-1183.
17. Hochreuther, S.; Puchta, R.; van Eldik, R. Thermodynamic and kinetic studies on novel dinuclear platinum(II) complexes containing bidentate N,N-donor ligands. *Inorg. Chem.* 2011, 50, 8984-8996.
18. Wang, J.; Williams, E. T.; Bourgea, J.; Wong, Y. N.; Patten, C. J. Characterization of recombinant human carboxylesterases: fluorescein diacetate as a probe substrate for human carboxylesterase 2. *Drug Metab. Dispos.* 2011, 39, 1329-1333.
19. Valiahdi, S. M.; Egger, A. E.; Miklos, W.; Jungwirth, U.; Meelich, K.; Nock, P.; Berger, W.; Hartinger, C. G.; Galanski, M.; Jakupec, M. A.; Keppler, B. K. Influence of extracellular pH on the cytotoxicity, cellular accumulation, and DNA interaction of novel pH-sensitive 2-amino-alcoholatoplatinum(II) complexes. *J. Biol. Inorg. Chem.* 2013, 18, 249-260.
20. Weaver, D. A.; Crawford, E. L.; Warner, K. A.; Elkhairi, F.; Khuder, S. A.; Willey, J. C. ABCC5, ERCC2, XPA and XRCC1 transcript abundance levels correlate with cisplatin chemoresistance in non-small cell lung cancer cell lines. *Mol. Cancer* 2005, 4, 18.
21. Barthel, B. L.; Zhang, Z.; Rudnicki, D. L.; Coldren, C. D.; Polinkovsky, M.; Sun, H.; Koch, G. G.; Chan, D. C.; Koch, T. H. Preclinical efficacy of a carboxylesterase 2-activated prodrug of doxazolidine. *J. Med. Chem.* 2009, 52, 7678-7688.
22. Martins, E. T.; Baruah, H.; Kramarczyk, J.; Saluta, G.; Day, C. S.; Kucera, G. L.; Bierbach, U. Design, synthesis, and biological activity of a novel non-cisplatin-type platinum-acridine pharmacophore. *J. Med. Chem.* 2001, 44, 4492-4496.
23. Zhang, Z.; Hatta, H.; Tanabe, K.; Nishimoto, S. A new class of 5-fluoro-2'-deoxyuridine prodrugs conjugated with a tumor-homing cyclic peptide CNGRC by ester linkers: synthesis, reactivity, and tumor-cell-selective cytotoxicity. *Pharm. Res.* 2005, 22, 381-389.

We claim:

1. The compound or a pharmaceutically acceptable salt of formula I

Formula I wherein each L independently is NH$_3$ or the Ls together with the platinum atom to which they are attached form a ring made up of an aliphatic diamine;

wherein

R' is a primary alcohol, a secondary alcohol or tertiary alcohol group containing between 1 and 10 carbon atom, or a primary, secondary, or tertiary alkyl group that contains a carboxylic acid group or an amido functionality; or an aryl group that contains an alcohol, carboxylic acid or amido group, or R' is an alkyl-aryl or an aryl group that contains an alcohol, carboxylic acid, or amido group which may additionally be optionally substituted with one or more substituents wherein said substituent is halo, hydroxyl, carboxyl, nitro, amino, C$_{1-6}$alkyl, C$_{2-6}$alkenyl, or C$_{2-6}$alkynyl;

n is 1 to 6;

m is 1 or 2;

and X is halo or NO$_3$.

2. The compound or a pharmaceutically acceptable salt of claim 1, wherein the Ls in the Formula I form a ring with the platinum compound to which they are joined to form a group that contains ethane-1,2-diamine, propane-1,3-diamine, trans-1,2-diaminocyclohexane (R,R, S,S, and R,S isomers), 2,3-diaminobutane (R,R, S,S, and R,S isomers).

3. The compound or a pharmaceutically acceptable salt of claim 1, wherein R' comprises a carboxylic acid group.

4. The compound or a pharmaceutically acceptable salt of claim 3, wherein R' comprises an alcohol.

5. The compound or a pharmaceutically acceptable salt of claim 3, wherein R' comprises an amido functionality.

6. The compound or a pharmaceutically acceptable salt of claim 3, wherein n is 1 to 3.

7. The compound or a pharmaceutically acceptable salt of claim 3, wherein n is 1.

8. The compound or a pharmaceutically acceptable salt of claim 3, wherein n is 3.

9. The compound or a pharmaceutically acceptable salt of claim 3, wherein X is Cl or $NO_3$.

10. The compound or a pharmaceutically acceptable salt of claim 3, wherein X is $NO_3$.

11. A pharmaceutical composition comprising the compound or a pharmaceutically acceptable salt of Formula I,

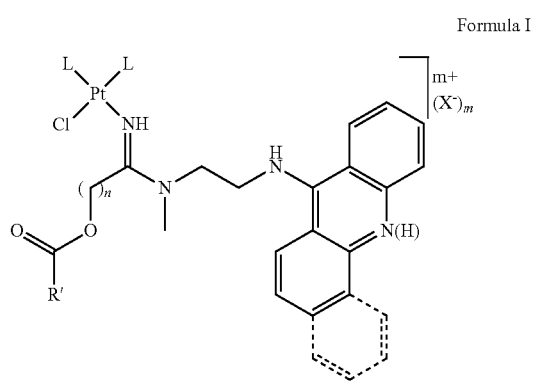

Formula I wherein each L independently is $NH_3$ or the Ls together with the platinum atom to which they are attached form a ring made up of an aliphatic diamine;
wherein R' is a primary alcohol, a secondary alcohol or tertiary alcohol group containing between 1 and 10 carbon atoms, or a primary, secondary, or tertiary alkyl group that contains a carboxylic acid group or an amido functionality; or an aryl group that contains an alcohol, carboxylic acid or amido group, or R' is an alkyl-aryl or an aryl group that contains an alcohol, carboxylic acid, or amido group which may additionally be optionally substituted with one or more substituents wherein said one or more substituents is/are halo, hydroxyl, carboxyl, nitro, amino, $C_{1-6}$alkyl, $C_{2-6}$alkenyl, or $C_{2-6}$alkynyl;
n is 1 to 6;
m is 1 or 2;
and X is halo or $NO_3$, and a pharmaceutically acceptable diluent, carrier, or excipient.

12. The pharmaceutical composition of claim 11, wherein the Ls in Formula I form a ring with the platinum compound to which they are joined to form a group that contains ethane-1,2-diamine, propane-1,3-diamine, trans-1,2-diaminocyclohexane (R,R, S,S, and R,S isomers), or 2,3-diaminobutane (R,R, S,S, and R,S isomers).

13. The pharmaceutical composition of claim 12, wherein R' comprises a carboxylic acid.

14. The pharmaceutical composition of claim 11, wherein R' comprises an alcohol.

15. The pharmaceutical composition of claim 13, wherein R' comprises an amido functionality.

16. The pharmaceutical composition of claim 13, wherein n is 1 to 3.

17. The pharmaceutical composition of claim 13, wherein X is Cl or $NO_3$.

18. A method of treating cancer comprising administering to a subject in need thereof a pharmaceutically acceptable dose of a compound of Formula I

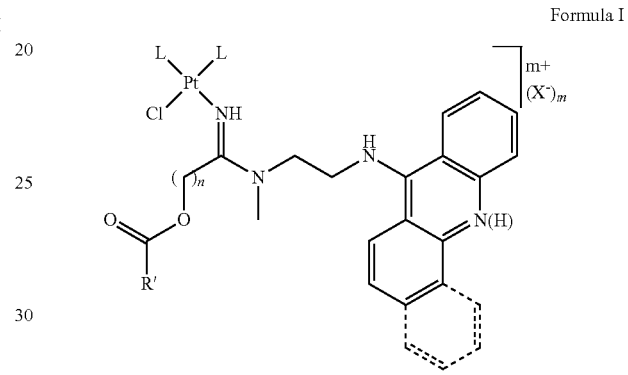

Formula I wherein each L independently is $NH_3$ or the Ls together with the platinum atom to which they are attached form a ring made up of an aliphatic diamine;
wherein R' is a primary alcohol, a secondary alcohol or tertiary alcohol group containing between 1 and 10 carbon atoms, or a primary, secondary, or tertiary alkyl group that contains a carboxylic acid group or an amido functionality; or an aryl group that contains an alcohol, carboxylic acid or amido group, or R' is an alkyl-aryl or an aryl group that contains an alcohol, carboxylic acid, or amido group which may additionally be optionally substituted with one or more substituents wherein said substituent is halo, hydroxyl, carboxyl, nitro, amino, $C_{1-6}$alkyl, $C_{2-6}$alkenyl, or $C_{2-6}$alkynyl;
n is 1 to 6;
m is 1 or 3;
and X is halo or $NO_3$.

19. The method of claim 18, wherein the cancer is lung adenocarcinoma.

20. The method of claim 18, wherein R' comprises an alcohol or carboxylic acid.

* * * * *

UNITED STATES PATENT AND TRADEMARK OFFICE
CERTIFICATE OF CORRECTION

PATENT NO. : 9,765,103 B2  
APPLICATION NO. : 15/321578  
DATED : September 19, 2017  
INVENTOR(S) : Ulrich Bierbach et al.

Page 1 of 1

It is certified that error appears in the above-identified patent and that said Letters Patent is hereby corrected as shown below:

In the Claims

At Column 38, Claim number 2, Line number 65, insert --or-- before "2,3-diaminobutane (R,R, S,S, and R,S isomers)"

At Column 40, Claim number 18, Line number 49, "m is 1 or 3;" should read as follows:
--m is 1 or 2;--

Signed and Sealed this
Twenty-third Day of July, 2019

Andrei Iancu
*Director of the United States Patent and Trademark Office*